US011944593B2

(12) United States Patent
Small-Howard et al.

(10) Patent No.: US 11,944,593 B2
(45) Date of Patent: Apr. 2, 2024

(54) MYRCENE-CONTAINING COMPLEX MIXTURES TARGETING TRPV1

(71) Applicant: GBS GLOBAL BIOPHARMA, INC., Ottawa (CA)

(72) Inventors: Andrea Small-Howard, Norwalk, CA (US); Helen Turner, Honolulu, HI (US)

(73) Assignee: GBS GLOBAL BIOPHARMA, INC., Ottawa (CA)

( * ) Notice: Subject to any disclaimer, the term of this patent is extended or adjusted under 35 U.S.C. 154(b) by 335 days.

(21) Appl. No.: 16/878,295

(22) Filed: May 19, 2020

(65) Prior Publication Data

US 2020/0390721 A1 Dec. 17, 2020

Related U.S. Application Data

(62) Division of application No. 15/986,316, filed on May 22, 2018, now Pat. No. 10,709,670.

(60) Provisional application No. 62/509,546, filed on May 22, 2017.

(51) Int. Cl.
| | | |
|---|---|---|
| *A61K 31/01* | (2006.01) | |
| *A61K 9/00* | (2006.01) | |
| *A61K 31/015* | (2006.01) | |
| *A61K 31/045* | (2006.01) | |
| *A61K 31/05* | (2006.01) | |
| *A61K 31/192* | (2006.01) | |
| *A61K 31/352* | (2006.01) | |
| *A61K 36/185* | (2006.01) | |
| *A61K 45/06* | (2006.01) | |
| *A61P 29/02* | (2006.01) | |

(52) U.S. Cl.
CPC ............ *A61K 31/01* (2013.01); *A61K 9/0014* (2013.01); *A61K 9/0019* (2013.01); *A61K 9/006* (2013.01); *A61K 9/0073* (2013.01); *A61K 31/015* (2013.01); *A61K 31/045* (2013.01); *A61K 31/05* (2013.01); *A61K 31/192* (2013.01); *A61K 31/352* (2013.01); *A61K 36/185* (2013.01); *A61K 45/06* (2013.01); *A61P 29/02* (2018.01); *A61K 2236/51* (2013.01)

(58) Field of Classification Search
None
See application file for complete search history.

(56) References Cited

U.S. PATENT DOCUMENTS

| | | | |
|---|---|---|---|
| 8,790,719 B2 | 7/2014 | Parolaro et al. | |
| 9,084,786 B2 | 7/2015 | Stokes | A61K 31/497 |
| 9,095,554 B2 | 8/2015 | Lewis | A01G 22/00 |
| 9,730,911 B2 | 8/2017 | Verzura et al. | |
| 10,709,670 B2 | 7/2020 | Small-Howard et al. | |
| 10,729,665 B2 | 8/2020 | Whalley et al. | |
| 10,774,288 B2 | 9/2020 | Elzinga et al. | |
| 11,260,044 B2 * | 3/2022 | Small-Howard | A61K 31/05 |
| 2007/0088072 A1 | 4/2007 | Di Marzo et al. | |
| 2007/0105086 A1 | 5/2007 | Qin et al. | |
| 2010/0249223 A1 | 9/2010 | Di Marzo et al. | |
| 2014/0271940 A1 | 9/2014 | Wurzer | |
| 2014/0298511 A1 | 10/2014 | Lewis | A01H 5/10 800/26 |
| 2016/0250270 A1 | 9/2016 | Wendschuh | A61K 31/122 514/454 |
| 2016/0279073 A1 | 9/2016 | Donsky et al. | |
| 2018/0169035 A1 | 6/2018 | Eyal | A61P 35/00 |
| 2018/0215705 A1 | 8/2018 | Xie et al. | |
| 2018/0338930 A1 | 11/2018 | Small-Howard et al. | |
| 2020/0155469 A1 | 5/2020 | Small-Howard et al. | |

FOREIGN PATENT DOCUMENTS

| | | | |
|---|---|---|---|
| CN | 101678059 A | 3/2010 | |
| CN | 103826621 A | 5/2014 | |
| CN | 105916492 A | 8/2016 | |
| CN | 107205960 A | 9/2017 | |
| JP | 2013-522184 A | 6/2013 | |
| JP | 2014-144942 A | 8/2014 | |
| JP | 6017330 B2 * | 10/2016 | A61K 31/01 |
| JP | 2017-501109 A | 1/2017 | |
| WO | WO 2006/065792 A2 | 6/2006 | |
| WO | WO 2007/047752 A1 | 4/2007 | |
| WO | WO 2011/110866 A1 | 9/2011 | |
| WO | WO 2014/159688 A1 | 10/2014 | |
| WO | WO 2015/042232 A1 | 3/2015 | |
| WO | WO 2016/094810 A2 | 6/2016 | |
| WO | WO 2016/138505 A1 | 9/2016 | |
| WO | WO 2017/158539 A1 | 9/2017 | |
| WO | WO 2018/071452 A1 | 4/2018 | |

(Continued)

OTHER PUBLICATIONS

SciFinder English language abstract (Database CAPLUS Acc. No. 1982:592915) of Li et al., Yaoxue Tongbao (1982), 17(5), pp. 304-305.*
Li et al., Yaoxue Tongbao (1982), 17(5), pp. 304-305.*
United States Office Action, U.S. Appl. No. 16/420,004, filed Jan. 11, 2021, 11 pages.
Carnevale, V. et al., "TRPV1: A Target for Rational Drug Design," Pharmaceuticals, vol. 9, No. 3, Aug. 23, 2016, pp. 1-20.

(Continued)

*Primary Examiner* — Brian J Davis
(74) *Attorney, Agent, or Firm* — Fenwick & West LLP

(57) ABSTRACT

Provided herein are pharmaceutical compositions that comprise myrcene, optionally in admixture with cannabinoids and other terpenes, typically substantially free of THC and THCA, for targeting TRPV1 receptors. Also provided are methods of using the pharmaceutical compositions to desensitize TRPV1 receptors in order to treat pain, cardiovascular diseases such as cardiac hypertrophy, overactive bladder, and chronic cough.

20 Claims, 28 Drawing Sheets

(56) References Cited

FOREIGN PATENT DOCUMENTS

| WO | WO 2018/170596 A1 | 9/2018 |
|---|---|---|
| WO | WO 2018/173049 A1 | 9/2018 |
| WO | WO 2018/217803 A3 | 11/2018 |
| WO | WO 2019/226833 A1 | 11/2019 |

OTHER PUBLICATIONS

Elokely, K. et al., "Understanding TRPV1 activation by ligands: Insights from the binding modes of capsaicin and resiniferatoxin," Proceedings of the National Academy of Sciences, vol. 113, No. 2, Dec. 30, 2015, pp. E137-E145.

European Patent Office, Office Action, EP Patent Application No. 18769850.1, dated Nov. 30, 2020, ten pages.

Hudson, D. et al., "Biopolymer nanoparticle production for controlled release of biopharmaceuticals," CRC Critical Reviews in Biotechnology, vol. 34, No. 2, Jan. 7, 2013, pp. 161-179.

Jansen, C. et al., "Myrcene and terpene regulation of TRPV1," Channels (Austin), vol. 13, No. 1, Aug. 26, 2019, pp. 344-366.

Lee, J.H. et al., "Structural insights into transient receptor potential vanilloid type 1 (TRPV1) from homology modeling, flexible docking, and mutational studies," Journal of Computer-Aided Molecular Design, vol. 25, No. 4, Mar. 30, 2011, pp. 317-327.

PCT International Search Report and Written Opinion, PCT Application No. PCT/US2020/039989, dated Oct. 12, 2020, 19 pages.

Rao, V.S.N et al., "Effect of myrcene on nociception in mice," J. Pharm. Pharmacol., vol. 42, Dec. 1990, pp. 877-878.

Starkus, J. et al., "Diverse TRPV1 Responses to Cannabinoids," Channels (Austin), vol. 13, No. 1, Jan. 1, 2019, pp. 172-191.

Bautista, D., et al., "Fire in the Hole: Pore Dilation of the Capsaicin Receptor TRPV1 ," Nature Neuroscience, 2008, vol. 11, pp. 528-529.

Bhattacharya, A., et al., "Pharmacology and Antitussive Efficacy of 4-(3-Trifluo ro methyl-Pyrid in-2-yl)-Piperazi ne-1-Ca rboxylic Acid (5-Trifluoro methyl-Pyrid in-2-yl)-Amide (JNJ17203212), a Transient Receptor Potential Vanilloid 1 Antagonist inGuinea Pigs," J. Pharmacol. Exp. Ther., Aug. 2007, vol. 323, pp. 665-674.

Booth, J. K. et al., "Terpene synthases from Cannabis sativa," PLOS One, Mar. 29, 2017, pp. 1-20.

Brito, R., et al., "TRPV1: A Potential Drug Target for Treating Various Diseases," Cells, 2014, vol. 3, 517-545.

Chung, M-K., et al., "TRPV1 Shows Dynamic Ionic Selectivity During Agonist Stimulation," Nature Neuroscience, 2008, vol. 11, pp. 555-564 (2008).

Dang, K., et al., "Cyclophosphamide-Induced Cystitis Reduces ASIC Channel but Enhances TRPV1 Receptor Function in Rat Bladder Sensory Neurons," J. Neurophysiol., 2013, vol. 110, pp. 408-417.

De Petrocellis, L. et al., "Effects of cannabinoids and cannabinoid-enriched Cannabis extracts on TRP channels and endocannabinoid metabolic enzymes," British Journal of Pharmacology, vol. 163, Dec. 22, 2010, pp. 1479-1495.

De Petrocellis, L., et al., "Cannabinoid Actions at TRPV Channels: Effects on TRPV3 and TRPV4 and Their Potential Relevance to Gastrointestinal Inflammation," Acta Physiol (Oxf)., Feb. 2012, vol. 204, No. 2, pp. 255-266.

De Petrocellis, L., et al., "Plant-Derived Cannabinoids Modulate the Activity of Transient Receptor Potential Channels of Ankyrin Type-1 and Melastatin type-8," J Pharmacol Exp Ther., Jun. 2008, vol. 325, No. 3, pp. 1007-1015.

Di Marzo, V. et al., "Endocannabinoids as Regulators of Transient Receptor Potential (TRP) Channels: A Further Opportunity to Develop New Endocannabinoid-Based Therapeutic Drugs," Current Medicinal Chemistry, 2010, pp. 1430-1449, vol. 17.

Doherty, M.J., et al., "Capsaicin Responsiveness and Cough in Asthma and Chronic Obstructive Pulmonary Disease," Thorax, 2000, vol. 55, pp. 643-649.

Dornelles, F.N., et al., "Role of CXCR2 and TRPV1 in functional, inflammatory and behavioural changes in the rat model of cyclophosphamide-induced haemorrhagic cystitis," Br. J. Pharmacol., 2014, vol. 171, pp. 452-467.

Groneberg, D.A., et al., "Increased Expression of Transient Receptor Potential Vanilloid-1 in Airway Nerves of Chronic Cough," Am. J. Respir. Crit. Care Med., 2004, vol. 170, pp. 1276-1280.

Iannotti, F.A. et al., "Nonpsychotropic Plant Cannabinoids, Cannabidivarin (CBDV) and Cannabidiol (CBD), Activate and Desensitize Transient Receptor Potential Vanilloid 1 (TRPV1) Channels in Vitro: Potential for the Treatment of Neuronal Hyperexcitability," ACS Chemical Neuroscience, 2014, pp. 1131-1141, vol. 5.

Lalloo, U.G., et al., "Capsazepine Inhibits Cough Induced by Capsaicin and Citric Acid but Not by Hypertonic Saline in Guinea Pigs," J. Appl. Physiol., 1995, vol. 79, pp. 1082-1087.

McLeod, R.L., et al., "TRPV1 Antagonists Attenuate Antigen-Provoked Cough in Ovalbumin Sensitized Guinea Pigs," Cough, 2006, vol. 2, No. 10, pp. 1-7.

Morales, P. et al., "Molecular Targets of the Phytocannabinoids: A Complex Picture," Phytocannabinoids, AD. Kinghorn et al. (eds.), Progress in the Chemistry of Organic Natural Products, 2017, pp. 103-131.

Nakajima, T., et al., "Cough Sensitivity in Pure Cough Variant Asthma Elicited Using Continuous Capsaicin Inhalation," Allergol. Int., 2006, vol. 55, pp. 149-155.

O'Connell, F., et al., "Capsaicin Cough Sensitivity Increases During Upper Respiratory Infection," Respir. Med., 1996, vol. 90, pp. 279-286.

PCT International Search Report and Written Opinion, PCT Application No. PCT/US2018/033956, dated Nov. 21, 2018, 17 pages.

Pecova, R., et al., "Cough Reflex Sensitivity Testing in in Seasonal Allergic Rhinitis Patients and Healthy Volunteers," J. Physiol. Pharmacol., 2008, vol. 59 (Suppl. 6), pp. 557-564.

Plevkova, J., et al., "Testing of Cough Reflex Sensitivity in Children Suffering from Allergic Rhinitis and Common Cold," J. Physiol. Pharmacol., 2006, vol. 57 (Suppl. 4), pp. 289-296.

Russo, E. B., "Taming THC: potential cannabis synergy and phytocannabinoid-terpenoid entourage effects," British Journal of Pharmacology, vol. 163, Aug. 2011, pp. 1344-1364.

Rybak, L.P., et al., "Ototoxicity," Kidney Int., 2007, vol. 72, pp. 931-935.

Trevisani, M., et al., "Antitussive Activity of lodo-Resiniferatoxin in Guinea Pigs," Thorax, 2004, vol. 59, pp. 769-772.

Wang, Z.Y., et al., "Lack of TRPV1 Inhibits Cystitis-Induced Increased Mechanical Sensitivity in Mice," Pain, 2008, vol. 139, pp. 158-167.

Costa, B. et al., "Vanilloid TRPV1 receptor mediates the antihyperalgesic effect of the nonpsychoactive cannabinoid, cannabidiol, in a rat model of acute inflammation," British Journal of Pahramcology, vol. 143, Aug. 16, 2004, pp. 247-250.

Cuñetti, L. et al., "Chronic Pain Treatment with Cannabidiol in Kidney Transplant Patients in Uruguay," Transplantation Proceedings, vol. 50, No. 2, Mar. 2018, pp. 461-464.

De Petrocellis, L. et al., "Non-$CB_1$, Non-$CB_2$ receptors for endocannabinoids, plant cannabinoids, and synthetic cannabimimetics: focus on G-protein-coupled receptors and transient receptor potential channels," J Neuroimmune Pharmacol, vol. 5, Oct. 22, 2009, pp. 103-121.

Gomes Paula-Freire, L. et al., "Ocimum gratissimum Essential Oil and Its Isolated Compounds (Eugenol and Myrcene) Reduce Neuropathic Pain in Mice," Planta Med 82(3), Feb. 2016, pp. 211-216.

Hunter, D. et al., "Synthetic transdermal cannabidiol for the treatment of knee pain due to osteoarthritis," Osteoarthritis and Cartilage, vol. 26, No. Supplement 1, Apr. 1, 2018, pp. S26.

Katsuyama, S. et al., "Intraplantar Injection of Linalool Reduces Paclitaxel-Induced Acute Pain in Mice," Biomedical Research, vol. 33, Iss. 3, Jul. 2012, pp. 175-181.

Mickle, A. D. et al., "Sensory TRP Channels: The Key Transducers of Nociception and Pain," Progress in Molecular Biology and Translational Science, Chapter Four, vol. 131, Mar. 1, 2015, pp. 73-118.

(56) References Cited

OTHER PUBLICATIONS

PCT International Search Report and Written Opinion, PCT Application No. PCT/US2019/033618, dated Sep. 13, 2019, 14 pages.
Planells-Cases, R. et al., "Small molecules targeting the vanilloid receptor complex as drugs for inflammatory pain," Drugs of the Future, vol. 28, Iss. 8, Aug. 2003, pp. 787-795.
United States Office Action, U.S. Appl. No. 16/420,004, dated Aug. 14, 2020, 22 pages.
United States Office Action, U.S. Appl. No. 15/986,316, dated May 15, 2019, 17 pages.
United States Office Action, U.S. Appl. No. 15/986,316, dated Dec. 26, 2019, 11 pages.
Danhier, F. et al., "PLGA-based nanoparticles: An overview of biomedical applications," Journal of Controlled Release, vol. 161, Feb. 4, 2012, pp. 505-522.
Durán-Lobato, M. et al., "Comparative study of chitosan- and PEG-coated lipid and PLGA nanoparticles as oral delivery systems for cannabinoids," J. Nanopart. Res., 17:61, Jan. 30, 2015, pp. 1-17.
Fein, A., "Nociceptors and the Perception of Pain," May 2014, pp. 1-1-8-14.
Martín-Banderas, L. et al., "In vitro and in vivo evaluation of A9-tetrahidrocannabinol/PLGA nanoparticles for cancer chemotherapy," International Journal of Pharmaceutics, vol. 487, Issues 1-2, pp. 2015-2212.
Russo, E.B., "Cannabidiol Claims and Misconceptions," Trends in Pharmacological Sciences, vol. 38, Iss. 3, Mar. 2017, pp. 198-201.
Anonymous, "Cannabis and chronic bladder pain", Oct. 4, 2018, four pages, [Online] [Retrieved on Mar. 20, 2023] Retrieved from the Internet: < URL: https://naturalcaregroup.com/cannabis-and-chronic-bladder-pain-uti-interstitial-cystitis/>.
Devi, A.S et al., "In silico drug designing approach to treat infectious disease using mangrove through docking analysis", Journal of Environmental Biology, vol. 37, No. 6, Sp. Iss. SI, Nov. 2016, pp. 1401-1406.
Do Nascimento Junior, J.A.A. et al., "Anti-biofilm potential of some plant volatile compounds against Proteus mirabilis", Planta Medica, vol. 82, No. Suppl 1, Dec. 2016, pp. S1-S381 (abstract only).

* cited by examiner

FIG. 3J
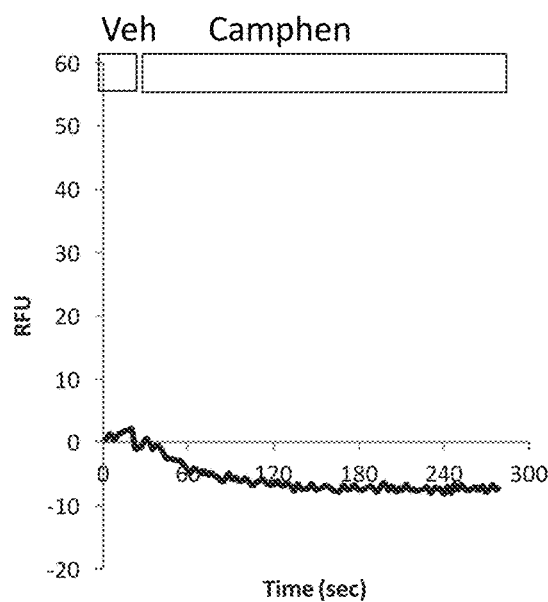
FIG. 3K
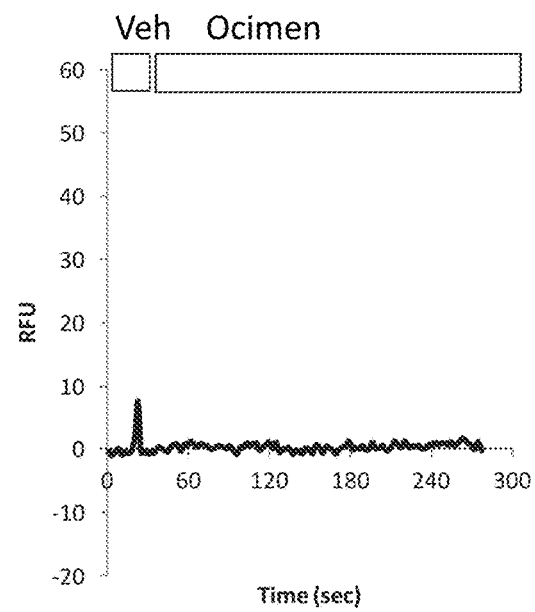
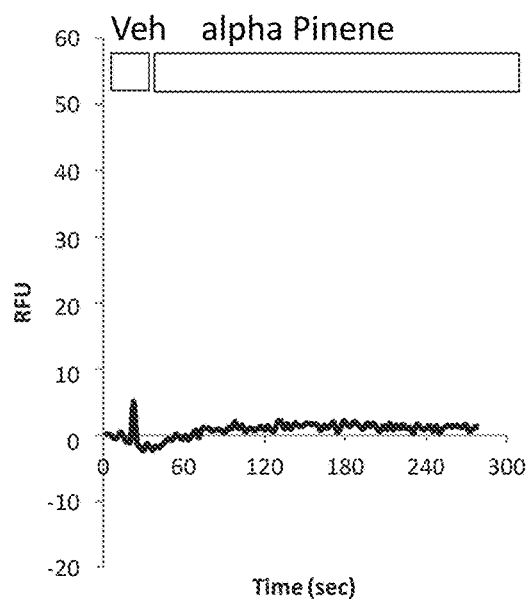
FIG. 3L

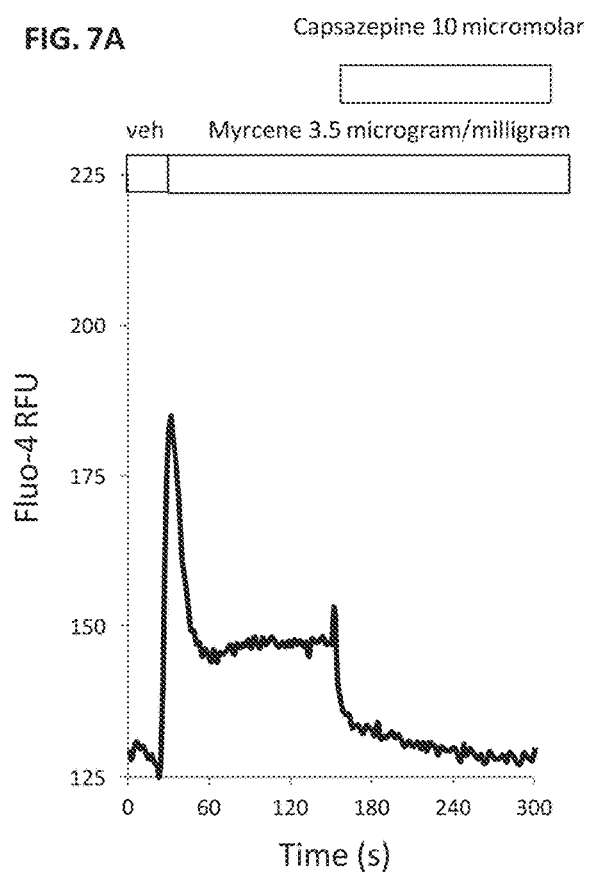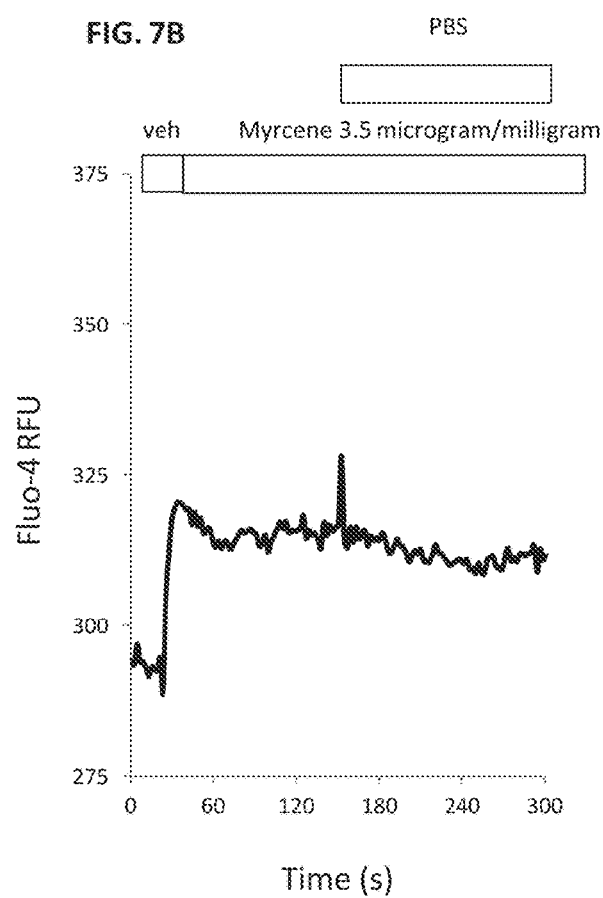

FIG. 11

| THERAPEUTIC TARGET DATABASE ENRICHMENT ANALYSIS ||||||||
|---|---|---|---|---|---|---|---|
| Myrcene InChI=1S/C10H16/ c1-5-10(4)8-6-7-9(2)3/h5,7H, 1,4,6,8H2,2-3H3 ||| Nerolidol InChI=1S/C15H26O/ c1-6-15(5,16)12-8-11-14(4)10-7 -9-13(2)3/h6,9,11,16H, 1,7-8,10,12H2,2-5H3 ||| *Cannabis sativa* |||
| Indication | p-value | targets | Indication | p-value | targets | Indication | p-value | targets |
| Analgesics | 3.30E-03 | 5 | Breast cancer | 2.04E-05 | 5 | Analgesics | 4.40E-08 | 32 |
| Noninsulin-Dependent Diabetes Mellitus | 1.19E-02 | 3 | Osteoporosis | 6.38E-05 | 3 | Asthma | 4.22E-03 | 17 |
| Pain | 3.63E-03 | 3 | Prostate cancer | 2.89E-02 | 2 | Alzheimer's Disease | 3.51E-04 | 16 |
| Cardiac Arrhythmias | 4.27E-03 | 2 | Neurodegenerative diseases | 9.31E-03 | 2 | Cardiovascular disease, unspecified | 7.97E-03 | 16 |
| Cancer, Unspecific | 8.62E-01 | 2 | Cardiovascular disease, unspecified | 2.80E-02 | 2 | Hypertension | 2.56E-04 | 15 |
| Inflammation | 2.42E-01 | 2 | Vitamin D deficiency | 1.01E-07 | 2 | Schizophrenia | 1.01E-07 | 13 |
| Obesity | 2.04E-01 | 2 | Vascular injury response | 8.93E-03 | 1 | Pain | 4.21E-05 | 12 |
| Epileptic Seizures | 1.29E-02 | 1 | Periodontitis | 8.93E-03 | 1 | Anxiety disorders | 4.79E-05 | 12 |
| Malignant Hyperthermia | 3.82E-02 | 1 | Atherosclerosis | 2.80E-02 | 1 | Atheroschlerosis | 1.47E-02 | 12 |
| Migraine | 1.45E-01 | 1 | Brain injury | 2.80E-02 | 1 | Heart failure | 3.51E-04 | 11 |

Input parameter score cutoff = 10
P value cutoff after Benjamini-Hochberg multiple testing correction
(Adjusted P-value) = 0.05

FIG. 12

| | MYRCENE | | | |
|---|---|---|---|---|
| Ion channel targets | Score | Frequency | Percentage of genes at this ranking | Function |
| KCNA1, KCNA10, KCNA2, KCNA3, KCNA4, KCNA5, KCNA6, KCNA7, KCNB1, KCNB2, KCNC1, KCNC2, KCNC3, KCND1, KCND2, KCND3 | >80 | 25/15937 | 0.15% | Potassium channels |
| AQP8 | | | | Aquaporin, water channels |
| KCNQ1 | >50 | 30/15937 | 0.18% | Potassium channels |
| KCNK4 | | | | |
| CACNA1D | >20 | 98/15937 | 0.60% | Voltage gated calcium channels |
| KCNE5 | | | | Potassium channels |
| SCN10A, SCN5A | | | | Sodium channels |
| KCNC4 | >8 | 107/15937 | | Potassium channels |
| AQP1 | >5 | 523/15937 | 3% | Aquaporin, water channels |
| CACNA1G, CACNA1H, CACNG2 | | | | Voltage gated calcium channels |
| CNGA1, CNGA2, CNGA3, CNGA4, CNGB1, CNGB3 | | | | Cyclic nucleotide gated calcium channels |
| HCN1, HCN2, HCN4 | | | | Hyperpolarization Activated Cyclic Nucleotide Gated Potassium Channel |
| TRPA1 | | | | Transient Receptor Potential non-selective cation channels |
| TRPM7 | | | | |
| TRPV1 | >2.6 | 552/15937 | | |
| TRPV2-6 | >2.3 | 15937/15937 | 100% | |
| TRPM1-6 | | | | |

FIG. 13

| \multicolumn{5}{c}{NEROLIDOL} | | | | |
|---|---|---|---|---|
| Ion channel targets | Score | Frequency | Percentage of genes at this ranking | Function |
| GABRA2, GABRD, GABRB1, GABRG3, GABRE, GABRA3, GABRG1, GABRP, GABRA4, GABRB2, GABRQ, GABRB3, GABRA5, GABRA6, GABRA1, GABRG2 | >8 | 43/16382 | 0.25% | GABA receptors |
| TRPV1 | >5 | 171/16382 | 1.00% | Transient Receptor Potential non-selective cation channels |
| SCN11A | >2.6 | 196/16382 | 1.20% | Sodium channels |

| TRPVI ligand | AUC Iono | AUC Iono after 24h exposure | used to factor | AUC Myrcene | AUC Myrcene after 24h exposure | AUC Capsaicin | AUC Capsaicin after 24h exposure | % supression |
|---|---|---|---|---|---|---|---|---|
| Myrcene | 128 | 94 |  | 66 | 32 |  |  | 52% |
| Capsaicin | 131 | 82 |  |  |  | 124 | 38 | 69% |

FIG. 15

| Artificial Strain A | Cannabinoid Mixture | Terpene Mixture |
|---|---|---|
| Cannabidivarin (CBDV) | Cannabidivarin (CBDV) | |
| Cannabichromene (CBC) | Cannabichromene (CBC) | |
| Cannabidiol (CBD) | Cannabidiol (CBD) | |
| Cannabidiolic Acid (CBDA) | Cannabidiolic Acid (CBDA) | |
| Cannabigerol (CBG) | Cannabigerol (CBG) | |
| Cannabigerolic Acid (CBGA) | Cannabigerolic Acid (CBGA) | |
| Cannabinol (CBN) | Cannabinol (CBN) | |
| alpha-Bisabolol | | alpha-Bisabolol |
| alpha-Humulene | | alpha-Humulene |
| alpha-Pinene | | alpha-Pinene |
| beta-Caryophyllene | | beta-Caryophyllene |
| beta-Myrcene | | beta-Myrcene |
| (+)-beta-Pinene | | (+)-beta-Pinene |
| Camphene | | Camphene |
| Limonene | | Limonene |
| Linalool | | Linalool |
| Nerolidol | | Nerolidol |

FIG. 18

Nerves are bundles of neurones

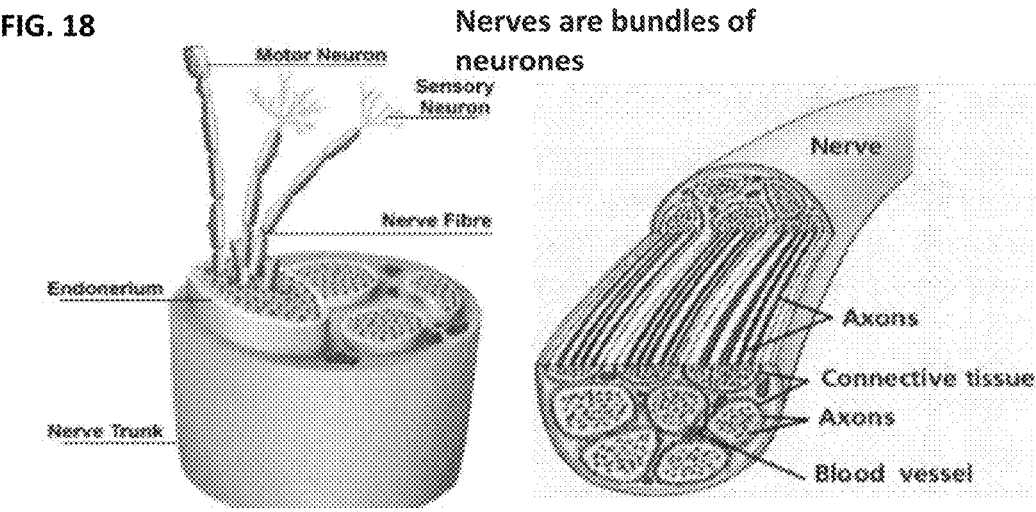

https://www.slideshare.net/clairegaukrodger/revision-the-nervous-system-16176977

Within a nocioceptive sensory neuron bundle, different neurones express different TRP channels, so they respond to different stimuli

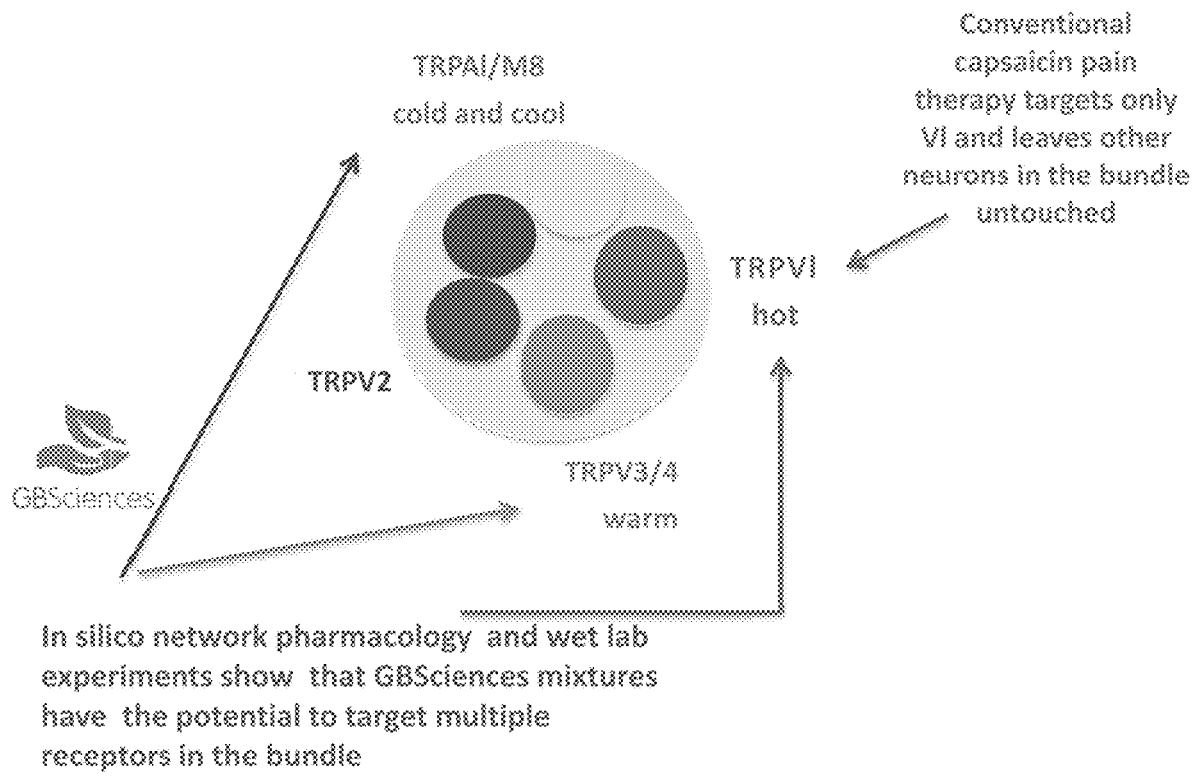

In silico network pharmacology and wet lab experiments show that GBSciences mixtures have the potential to target multiple receptors in the bundle

MYRCENE-CONTAINING COMPLEX MIXTURES TARGETING TRPV1

CROSS REFERENCE TO RELATED APPLICATIONS

This application is a continuation of co-pending U.S. application Ser. No. 15/986,316, filed on May 22, 2018, which claims priority benefit to U.S. Provisional Application No. 62/509,546 filed on May 22, 2017, which are incorporated by reference in its entirety.

1. BACKGROUND

Channels of the Transient Receptor Superfamily (TRP), such as TRPV1, TRPM8 and TRPA1, are non-selective cation channels that conduct calcium and sodium into a range of cell types in mammals. They are present on sensory neurons, and were initially identified as having a role in nociception because of their responsiveness at the molecular level to plant secondary metabolites that are nociomimetic (e.g., capsaicin) and to compounds that are otherwise pungent and mimic burning or cooling sensations (e.g., allicin, cinnamaldehyde, menthol).

Because of their role in nociception, TRP channels have been identified as targets for treating pain disorders. Both antagonism and agonism of the TRP channel have been exploited for pain management. For example, TRPV1 antagonists have utility in acute analgesia. For chronic pain management, TRPV1 agonists are typically used. This latter strategy exploits the fact that continued TRPV1 receptor agonism causes desensitization at the cell surface (receptor internalization, degradation and recycling). Prolonged agonism of TRPV1 also leads to calcium and sodium cationic overload of the TRPV1-containing sensory neuron, leading to cell death.

In practice, the use of TRPV1 agonists to effect desensitization involves topical application of high levels of a well-known TRPV1 agonist, capsaicin, repeatedly over time to the affected area. This therapeutic approach has the benefit of efficacy and low cost. However, it also has weaknesses.

First, high affinity and high specificity TRPV1 agonists target only TRPV1-containing nociceptors, leaving other sensory neurons and TRP channels involved in pain untouched. Second, use of high affinity and high specificity TRPV1 agonists such as capsaicin causes high levels of discomfort during initial treatment, in the period prior to desensitization. It is for this reason that post-herpetic pain is currently not addressable using TRPV1-mediated desensitization due to the highly irritant nature of the therapy on sensitive areas such as the gastric mucosa and reproductive tract mucosa. Third, capsaicin-mediated desensitization treatments are limited to topical use; visceral pain, headache and certain musculoskeletal pain disorders are not addressed by this therapy.

There is, therefore, a need for therapeutic TRPV1 ligands, such as TRPV1 agonists, that are lower affinity than capsaicin. Such lower affinity ligands should cause reduced pain during desensitization, thereby allowing topical treatment of sensitive body areas. There is a need for TRPV1 ligands with broader target specificity, able to target multiple types of TRP-bearing nociceptors, thereby improving the degree of tissue desensitization. There is also a need for TRPV1 ligands suitable for systemic administration in addition to topical application.

Such new medications would also be useful for the treatment of various diseases associated with TRPV1 other than pain. While TRP channels were first shown to be involved in pain and nociception, they now known to have various other physiological roles, suggesting that they can be a target for treatment of other diseases. For example, TRP channels have been identified as a target for treatment of cardiovascular disease; targeted pharmacological inhibition of TRPV1 has been shown to significantly diminish cardiac hypertrophy in a mouse model. See U.S. Pat. No. 9,084,786. Chronic downregulation of TRPV1 levels by receptor desensitization with a TRPV1 agonist would therefore be expected to similarly protect, and potentially rescue, cardiac hypertrophy and its associated symptoms and outcomes (cardiac remodeling, cardiac fibrosis, apoptosis, hypertension, or heart failure). However, there is currently no TRPV1 agonist suitable for systemic administration and suitable for chronic downregulation of TRPV1 in a visceral organ, and there is therefore a need to develop such approaches in an analogous manner to the chronic pain approaches described above.

Thus, there exists a need to find new compounds that act as TRPV1 antagonists and TRPV1 agonists. Such new compounds would provide novel and more effective ways of treating various diseases associated with the TRPV1 channel, including pain disorders and cardiovascular diseases.

2. SUMMARY

*Cannabis* has been used for millennia to provide analgesia and treat various types of pain. As described more fully in the experimental Examples below, using complex mixtures of terpenes and cannabinoids modeled after a known medicinal *Cannabis* chemo-profile, we have now demonstrated that *Cannabis* exerts its anti-nociceptive effects at least in part through the TRPV1 receptor. We have further demonstrated that myrcene contributes significantly to the observed TRPV1 agonism, and that like capsaicin, causes TRPV1 desensitization after prolonged exposure.

We have also demonstrated that other terpenes and cannabinoids present in the complex mixture, including those that do not demonstrate significant TRPV1 agonist activity on their own, act in combination to increase the efficacy of myrcene. We have shown that the *Cannabis*-like 'entourage' functions, at least in part, to block the multidrug resistance protein-mediated export of the bioactive ligand, myrcene.

Finally, to assess the broader therapeutic potential of myrcene, we generated a target analysis and disease-prediction network for myrcene using a proprietary in silico prediction approach, termed the GB Sciences' Network Pharmacology Platform ("NPP"). The presence of multiple TRP channels in the network additional to TRPV1 indicates that efficacy of myrcene will likely extend beyond TRPV1 to other nociceptive neurons in which the primary pain conduction channel is a distinct TRP receptor.

Accordingly, in a first aspect, pharmaceutical compositions are provided. The pharmaceutical composition comprises myrcene and a pharmaceutically acceptable carrier or diluent. The composition optionally includes at least one cannabinoid and/or at least one terpene other than myrcene. The composition comprises no more than 20 different species of cannabinoid and terpene compounds, and is substantially free of THC.

In some embodiments, the composition comprises no more than 15 species of cannabinoid and terpene compounds, no more than 10 species of cannabinoid and terpene compounds, or no more than 5 species of cannabinoid and terpene compounds.

In some embodiments, myrcene is present in an amount that is at least 10% (w/w) of the total content of cannabinoids and terpenes, at least 20% (w/w) of the total content of cannabinoids and terpenes, or at least 25% (w/w) of the total content of cannabinoids and terpenes. In certain embodiments, myrcene is present in an amount that is at least 50% (w/w), 75% (w/w), or at least 90% (w/w) of the total content of cannabinoids and terpenes.

In some embodiments, the pharmaceutical composition comprises nerolidol. In certain of these embodiments, nerolidol is present in an amount that is at least 2% (w/w) of the total content of cannabinoids and terpenes, at least 2.5% (w/w) of the total content of cannabinoids and terpenes, or even at least 5% (w/w), 7.5% (w/w), or 10% (w/w) of the total content of cannabinoids and terpenes.

In some embodiments, the pharmaceutical composition comprises cannabigerolic acid (CBGA). In certain embodiments, CBGA is present in an amount that is at least 10% (w/w) of the total content of cannabinoids and terpenes. In particular embodiments, CBGA is present in an amount that is at least 15% (w/w), 20% (w/w), or 25% (w/w) of the total content of cannabinoids and terpenes.

In some embodiments, the pharmaceutical composition comprises cannabidiol (CBD). In certain embodiments, CBD is present in an amount that is at least 2.5% (w/w) of the total content of cannabinoids and terpenes. In particular embodiments, CBD is present in an amount that is at least 5% (w/w), 7.5% (w/w), or 10% (w/w) of the total content of cannabinoids and terpenes.

In some embodiments, the pharmaceutical composition comprises cannabidivarin (CBDV). In certain embodiments, CBDV is present in an amount that is at least 5% (w/w) of the total content of cannabinoids and terpenes. In particular embodiments, CBDV is present in an amount that is at least 7.5% (w/w) or 10% (w/w) of the total content of cannabinoids and terpenes.

In some embodiments, the pharmaceutical composition comprises cannabichromene. In certain embodiments, cannabichromene is present in an amount that is at least 1% (w/w), 1.5 (w/w), 2% (w/w), or 2.5% (w/w) of the total content of cannabinoids and terpenes.

In some embodiments, the pharmaceutical composition comprises cannabidiolic acid (CBDA). In various embodiments, CBDA is present in an amount that is at least 2.5% (w/w) of the total content of cannabinoids and terpenes. In certain embodiments, CBDA is present in an amount that is at least 5% (w/w) or 7.5% (w/w) of the total content of cannabinoids and terpenes.

In some embodiments, the pharmaceutical composition comprises cannabigerol (CBG). In certain embodiments, CBG is present in an amount that is at least 2.5% (w/w), or 5% (w/w) of the total content of cannabinoids and terpenes.

In various embodiments, myrcene is present in the pharmaceutical composition at a concentration of 0.025%-5% (w/v). In some embodiments, myrcene is present in the composition at a concentration of 0.025%-2.5% (w/v), or 0.025%-1% (w/v).

In currently preferred embodiments, the cannabinoid compounds and terpene compounds other than myrcene, if present, are present in amounts that are effective to increase myrcene-dependent TRPV1 calcium flux.

In various embodiments, the pharmaceutical composition is formulated for topical administration. In various embodiments, the pharmaceutical composition is formulated for oral, buccal, or sublingual administration. In some embodiments, the pharmaceutical composition is formulated for intravenous, intramuscular, or subcutaneous administration.

In certain embodiments, the pharmaceutical composition is formulated for administration by inhalation. In particular embodiments, the pharmaceutical composition is formulated for administration by vaporizer, nebulizer, or aerosolizer.

In another aspect, methods of effecting TRPV1 desensitization in cells of a mammalian subject are provided. The method comprises administering to the subject a myrcene-containing pharmaceutical compositions as described herein in an amount, by a route of administration, and for a time sufficient to cause TRPV1 desensitization in cells within the subject.

In certain embodiments of the method, the cells are nociceptors. In particular embodiments, the nociceptors are peripheral nociceptors. In particular embodiments, the nociceptors are visceral nociceptors.

In various embodiments of the method, the pharmaceutical composition is administered topically.

In some embodiments, the pharmaceutical composition is administered systemically. In certain systemic administration embodiments, the pharmaceutical composition is administered intravenously. In other embodiments, the pharmaceutical composition is administered subcutaneously. In other embodiments, the pharmaceutical composition is administered by inhalation. In some embodiments, the pharmaceutical composition is administered by multiple routes of administration.

In another aspect, methods are provided for treating pain in a mammalian subject. The method comprises administering to the subject a myrcene-containing pharmaceutical compositions as described herein in an amount, by a route of administration, and for a time sufficient to cause TRPV1 desensitization in nociceptors within the subject.

In some embodiments, the nociceptors are peripheral nociceptors, and the pharmaceutical composition is administered topically. In some embodiments, the nociceptors are visceral nociceptors, and the pharmaceutical composition is administered systemically.

In some embodiments, the pain is neuropathic pain. In particular embodiments, the neuropathic pain is diabetic peripheral neuropathic pain. In certain embodiments, the pain is post-herpetic neuralgia.

In various embodiments, the pharmaceutical composition is administered at least once a day for at least 3 days, at least 5 days, or at least 7 days. In particular embodiments, the pharmaceutical composition is administered at least once a day for more than 7 days.

In various embodiments, the pharmaceutical composition is administered at a dose, by a route of administration, and on a schedule sufficient to maintain effective levels of myrcene at the nociceptors for at least 3 days, at least 5 days, or at least 7 days.

In another aspect, methods are provided for treating cardiac hypertrophy in a mammalian subject. The method comprises administering to a subject having cardiac hypertrophy an anti-hypertrophic effective amount of a myrcene-containing pharmaceutical composition as described herein.

In typical embodiments, the pharmaceutical composition is administered systemically. In particular embodiments, the pharmaceutical composition is administered intravenously. In certain embodiments, the pharmaceutical composition is administered subcutaneously. In certain embodiments, the pharmaceutical composition is administered by inhalation. In certain embodiments, the pharmaceutical composition is administered orally.

In a related aspect, methods are provided for the prophylactic treatment of cardiac hypertrophy in a mammalian subject. The method comprises administering to a subject at risk of cardiac hypertrophy an anti-hypertrophic effective amount of a myrcene-containing pharmaceutical composition as described herein.

In a further aspect, methods of treating overactive bladder in a mammalian subject are provided. The method comprises administering to the subject a therapeutically effective amount of a myrcene-containing pharmaceutical composition as described herein.

In some embodiments, the pharmaceutical composition is administered systemically. In some embodiments, the pharmaceutical composition is administered by bladder irrigation.

In a yet further aspect, methods are provided for treating refractory chronic cough in a mammalian subject. The method comprises administering to a subject with chronic cough a therapeutically effective amount of a myrcene-containing pharmaceutical composition as described herein.

In some embodiments, the pharmaceutical composition is administered systemically. In some embodiments, the pharmaceutical composition is administered by inhalation.

As further described herein, methods are provided for enhancing the specific activity of a primary therapeutic agent, such as myrcene, through the addition of a proprietary mixture of cannabinoids and terpenes. Without wishing to be bound by theory, the additional compounds included in the active pharmaceutical ingredient inhibit common molecular export pathways, mediated by the Multi-drug Resistance Protein, MRP, transporter family, that are constitutively active in the target cell types.

In typical embodiments, the myrcene-containing complex mixtures contain compounds identified from *Cannabis* spp., broadly divided into two groups: (a) cannabinoids, and (b) terpenes. The concentrations of these compounds in the plant vary widely across *Cannabis* strains, cultivars, time, cultivation methods and environmental conditions, etc. Complex interactions among these compounds means that translation from plant to clinic is not straightforward, and underscores the need for deconstruction, optimization and reconstruction of mixtures of a therapeutically desirable composition. The present disclosure meets the need by providing the methods for identifying the therapeutically desirable composition by deconstruction, optimization and reconstruction processes as well as the composition identified by the methods.

As summarized above, the pharmaceutical compositions described herein are effective for the treatment of various diseases involving TRP channels, including but not limited to TRPV1. In some aspects, the pharmaceutical compositions can be used for the treatment and prevention of chronic and acute pain in humans and other mammals, for the treatment of cardiac hypertrophy, for prophylactic treatment of cardiac hypertrophy, for treating other aspects of cardiovascular disease, for treating overactive bladder, and for treating chronic cough.

In particular, the myrcene-containing pharmaceutical compositions disclosed herein provide novel and effective ways of treating and preventing various pain disorders. Such disorders include, but are not limited to, migraine and other serious headaches, arthritis and other joint pain, fibromyalgia, endometriosis, irritable bowel syndrome, chronic interstitial cystitis, vulvodynia, trauma or postsurgical pain, lower back pain and other musculoskeletal disorders, temporomandibular joint disorder, shingles, sickle cell disease, heart disease (angina), cancer, stroke, diabetes, post-herpetic pain, and others.

The mixtures are expected to replace or supplement other pain approaches available in the art. First, currently available approaches cannot target ion channels such as TRPV1 in both dermal and visceral or internal locations. Second, compounds and mixtures of the present invention activate TRP channels through the use of complex mixtures derived from the *Cannabis* plant secondary metabolome, by decreasing ligand efflux via pathways such as multidrug resistance protein mediated export, providing the potential for lower dose schedules of the primary ligand to be deployed. Third, the potential for TRPV1-mediated approaches to post-herpetic pain which require exposure of sensitive mucosa to highly irritant doses of capsaicin may be improved upon with the pharmaceutical compositions described herein.

Furthermore, the compounds and their mixtures in the present invention are expected to replace or supplement marijuana-based medicines available in the art, which are still imperfect, as follows: First, the method 'homes in' on desirable compositions of cannabinoids/terpenes for pain therapy, which could later be presented either in bespoke synthetic compositions or in judging/ranking the merits of certain naturally occurring *Cannabis* strains/cultivars for therapeutic applications. These are an improvement over current prescribing or strain selection methodologies, which are based largely on anecdotal evidence. Second, the method provides for the design of synthetic compositions which can be manufactured consistently and in a contaminant free manner, which is an improvement over the current state of the medical marijuana production process where batch-to-batch consistency is not assured (due to differences in growing conditions, genetic/epigenetic and metabolic variance between plants and variations in extraction methods) and where microbial and chemical contamination is a persistent issue. Third, the single compounds and bespoke mixtures presented here are free of the major psychoactive cannabinoid, delta-9 tetrahydrocannabinol (THC). These mixtures therefore present a decreased regulatory and ethical burden when compared to medical marijuana as it is commonly available. Moreover, since any addictive or reinforcing potential for *Cannabis* is likely to reside in the presence of the major psychoactive ingredient, the bespoke mixtures presented here improve over opioid-based therapeutics for pain based on a decreased likelihood for patient addiction. Accordingly, the present invention has great value for the treatment and prevention of various pain disorders.

In addition, the myrcene-containing mixtures disclosed herein provide novel methods for treating cardiovascular disease including cardiac hypertrophy, including processes of cardiac remodeling, cardiac fibrosis, apoptosis, hypertension, or heart failure.

The compounds and mixtures disclosed herein are expected to replace or supplement other cardiovascular therapy approaches available in the art, which are still imperfect as follows: (1) the need for therapeutic approaches to downregulating TRPV1 in visceral locations, and (3) the need for therapeutic approaches to diminishing or reversing the processes of cardiac remodeling, cardiac fibrosis, apoptosis, hypertension, or heart failure. Accordingly, the present invention has potential value for the treatment and prevention of various cardiovascular disorders.

These and other aspects of the invention are described in further detail below.

3. BRIEF DESCRIPTION OF THE DRAWINGS

FIG. 1 illustrates that the inducible expression of TRPV1 in a non-TRPV1 containing cell type confers capsaicin-sensitive calcium flux responses upon the cells. Here, HEK cells transfected with a rat TRPV1 gene under the control of a tetracycline-inducible promoter were induced to transcribe the TRPV1 gene and synthesize TRPV1 protein through the application of tetracycline for 16 h at 1 micromolar. This establishes that the experimental system used in the following studies clearly, and specifically, reports TRPV1-specific calcium fluxes, since capsaicin is a specific ligand for TRPV1.

FIG. 2A-2C illustrate that terpenes contribute significantly to calcium fluxes via TRPV1 induced by *Cannabis*-derived mixtures of cannabinoids and terpenes. FIG. 2A shows calcium influx (relative fluorescence unit, "Fluo-4 RFU") over time (in seconds, "s") in HEK cells transfected with a construct encoding TRPV1, first without stimulus ("NS"), then after application of vehicle ("veh"), and after application of Strain A Mixture ("Strain mixture"). FIG. 2B shows calcium influx in TRPV1-expressing HEK cells after application of a mixture that includes only the cannabinoids present in the Strain A Mixture ("Cannabinoid Mixture"). FIG. 2C shows calcium influx in TRPV1-expressing HEK cells after application of a mixture that includes only the terpenes present in the Strain A Mixture ("Terpene Mixture").

FIGS. 3A-3L illustrate that individual terpenes differentially contribute to calcium fluxes induced by the Terpene Mixture via TRPV1. FIG. 3A presents calcium influx over time in HEK cells transfected with a construct encoding TRPV1 without stimulus ("NS"), after application of vehicle ("veh"), and after application of the Terpene Mixture ("all terpenes"). FIGS. 3B-3L graph baseline-subtracted calcium influx over time in the TRPV1-expressing HEK cells separately for each of the terpenes present in the Terpene Mixture used in FIG. 3A.

FIG. 4 illustrates that myrcene contributes significantly to TRPV1-mediated calcium responses seen with the Terpene Mixture ("Terpenes"), but does not constitute 100% of the signal. Data were obtained from HEK cells transfected with and inducibly expressing TRPV1.

FIGS. 5A-5C illustrate that the measured calcium responses depend wholly or in part on the presence of the TRPV1 ion channel. FIG. 5A shows calcium influx over time in HEK wild type cells ("HEK wild type") and in HEK cells transfected with and induced to express TRPV1 through the application of tetracycline (1 μM for 16 hours) ("HEK+TRPV1") after application of the complete Strain A mixture. FIG. 5B shows calcium influx over time in HEK wild type cells and in HEK+TRPV1 cells after application of a mixture that includes only the cannabinoids present in the Strain A Mixture ("Cannabinoid Mixture"). FIG. 5C shows calcium influx over time in HEK wild type cells and in HEK+TRPV1 cells after application of a mixture that includes only the terpenes present in the Strain A Mixture ("Terpene Mixture"). All data are vehicle subtracted.

FIGS. 6A-6C illustrate that the myrcene-induced calcium influx depends wholly or in part on the presence of the TRPV1 ion channel. FIGS. 6A-6B show calcium influx over time in HEK wild type cells ("HEK wild type") and in HEK+TRPV1 cells after application of myrcene at various concentrations: 3.5 μg/mg (FIG. 6A), 1.75 μg/mg (FIG. 6B), 0.875 μg/mg (FIG. 6C), and 0.43 μg/mg (FIG. 6D). All data are baseline subtracted.

FIGS. 7A-7B illustrates that the measured myrcene-induced calcium influx responses are inhibited by a specific pharmacological inhibitor of the TRPV1 ion channel. FIG. 7A shows calcium influx in TRPV1-expressing HEK cells over time (in seconds) in response to application of vehicle ("veh"), myrcene at 3.5 μg/ml, and further addition of the TRPV1 inhibitor, capsazepine (10 μM). FIG. 7B shows calcium influx in TRPV1-transfected HEK cells over time (in seconds) in response to application of vehicle ("veh"), myrcene at 3.5 μg/ml, and further addition of phosphate-buffered saline ("PBS") instead of capsazepine. Data are baseline-subtracted.

FIGS. 8A-8D illustrate that when myrcene is applied in the absence of external calcium, at high concentrations it can induce TRPV1-dependent calcium release from internal stores. FIGS. 8A-D present cytosolic calcium influxes over time in transfected HEK cells expressing TRPV1 ("HEK TRPV1") or a wild-type HEK cells ("HEK wild type") in response to various concentrations of myrcene—3.5 μg/ml (FIG. 8A), 1.75 μg/ml (FIG. 8B), 0.875 μg/ml (FIG. 8C) and 0.43 μg/ml (FIG. 8D) of myrcene. Experiments were conducted in the absence of external calcium in the medium. All data are baseline subtracted.

FIGS. 9A-9G illustrate that cannabinoids differentially contribute to calcium fluxes via TRPV1. FIGS. 9A-9G show calcium influx over time (seconds, "sec") in HEK wild type cells and HEK cells expressing TRPV1 individually for each of the cannabinoids present in the Cannabinoid Mixture tested in FIG. 2B. All stimuli were added at 20 seconds. All data are baseline subtracted.

FIG. 10 illustrates that the specific activity of bioactive ligands such as myrcene may be enhanced by co-incubation of a *Cannabis*-like 'entourage', through blocking of multi-drug resistance protein-mediated export of the bioactive ligand. Multi-drug Resistance Protein (MRP)-mediated efflux rates of the fluorescent marker CFDA were evaluated by flow cytometry in the presence of vehicle only ("veh"), the known MRP inhibitor, chloroquine ("Chloroquine"), and in the presence of "CBMIX", a mixture of all of the cannabinoids and terpenes other than myrcene in the Strain A Mixture. These data suggest that if used as an adjunct to a primary therapeutic compound, co-application of a plurality of cannabinoids and/or terpenes would tend to delay the efflux of the therapeutic compound from the cell and this increase the specific activity of the primary therapeutic compound per unit dose.

FIG. 11 illustrates that TTD Therapeutic Target Data Base Enrichment Analysis tends to prioritize Myrcene over Nerolidol for development in pain and cardiovascular areas. In addition, myrcene contributes significantly to the predicted disease target set for native *Cannabis*.

FIG. 12 illustrates that diverse ion channel targets are predicted for direct or indirect modulation by myrcene.

FIG. 13 illustrates that limited ion channel targets or CNS-active targets are predicted for direct or indirect modulation by nerolidol.

Figures 14A, 14B:
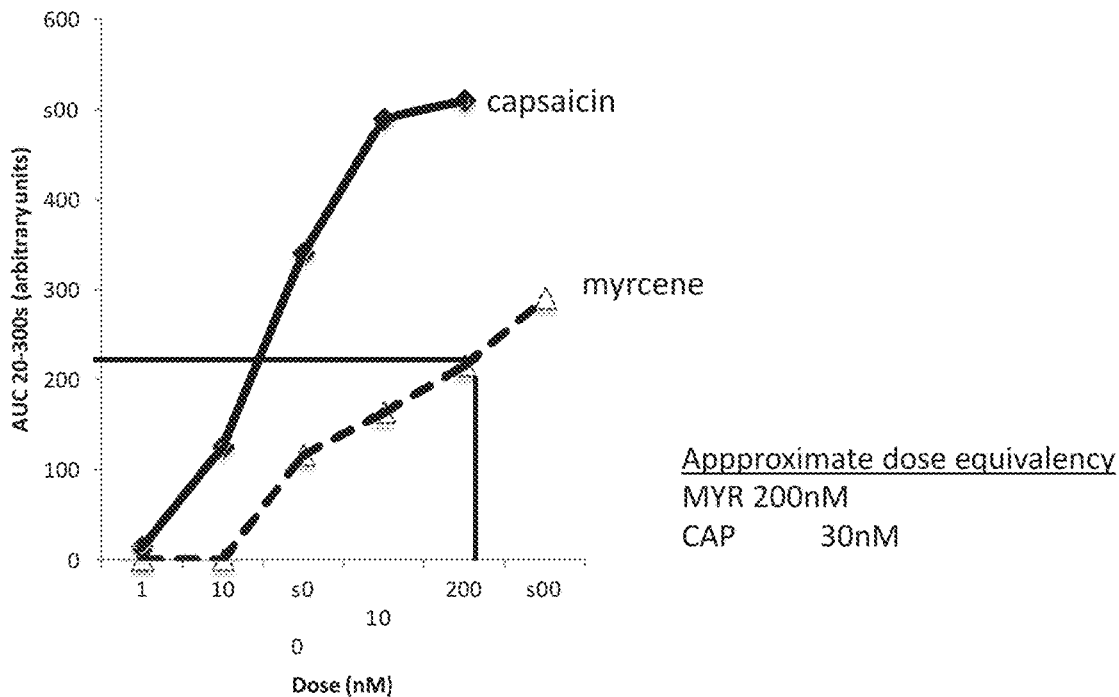

FIGS. 14A-14B illustrate the comparative desensitization patterns for TRPV1 initiated by capsaicin versus myrcene. FIG. 14A graphs dose-dependent calcium responses to various concentrations of myrcene and capsaicin by plotting area under the calcium influx curves (AUC) measured 20 to 300 seconds after application of the respective TRPV1 agonist (y-axis) with respect to corresponding concentrations (x-axis). FIG. 14B provides AUCs of calcium influx curves measured in TRPV1-expressing HEK cells before and 24 hours after application the ionophore ionomycin, myrcene or capsaicin. The percentage suppression in the values measured before and after the application are also provided (Supp %).

FIG. 15 lists the compounds used in the experiments described.

Figure 16A:
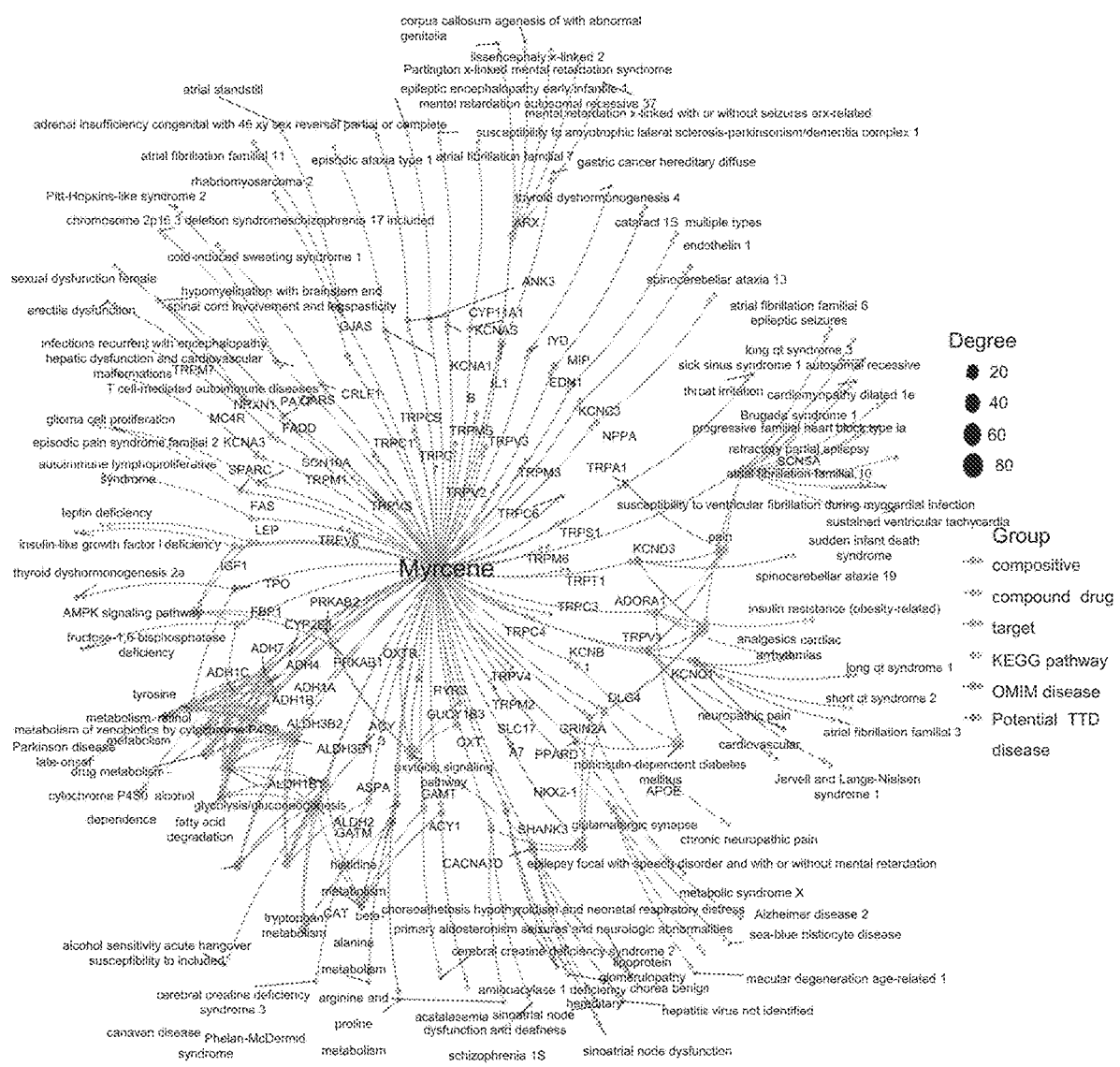
Figure 16B:
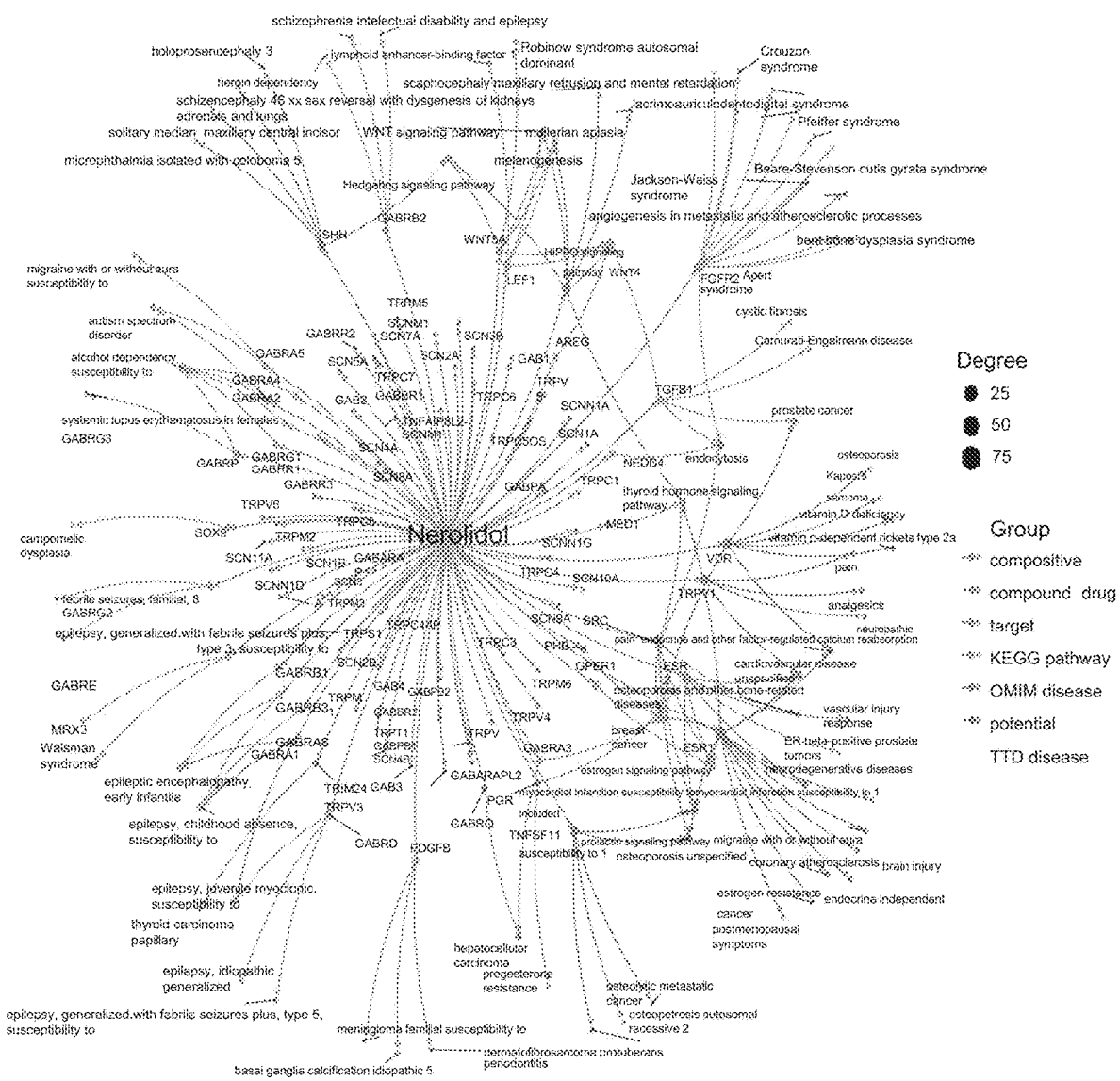

FIGS. 16A-16B show a target analysis and disease-prediction network for two terpenes, myrcene (FIG. 16A) and nerolidol (FIG. 16B). The data were generated in silico using GB Sciences' Network Pharmacology Platform ("NPP"). The presence of multiple TRP channels in the network indicates that efficacy of myrcene will likely extend beyond TRPV1 to other nociceptive neurons in which the primary pain-conducting channel is a distinct TRP.

Figure 10:
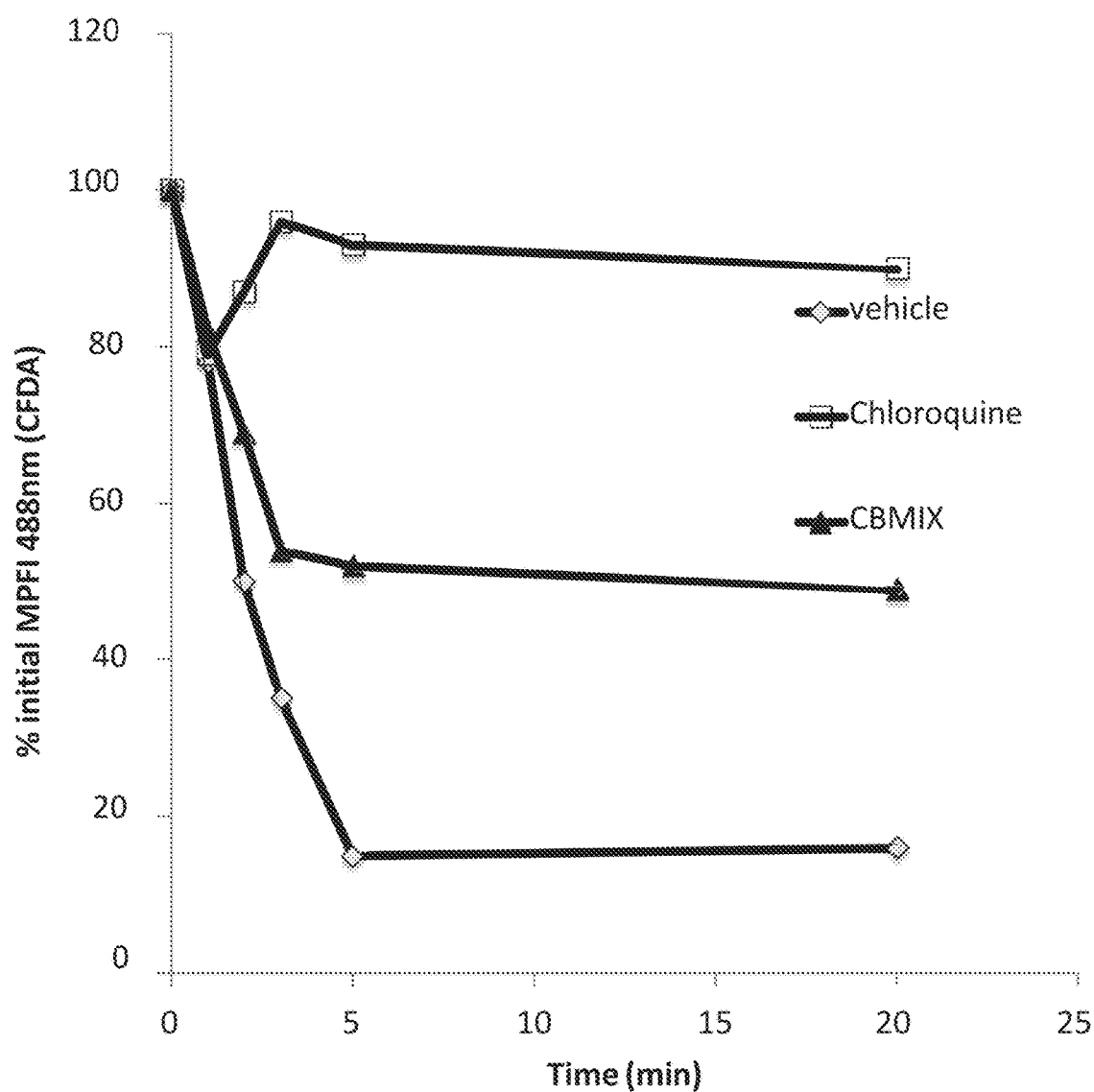
Figure 17:
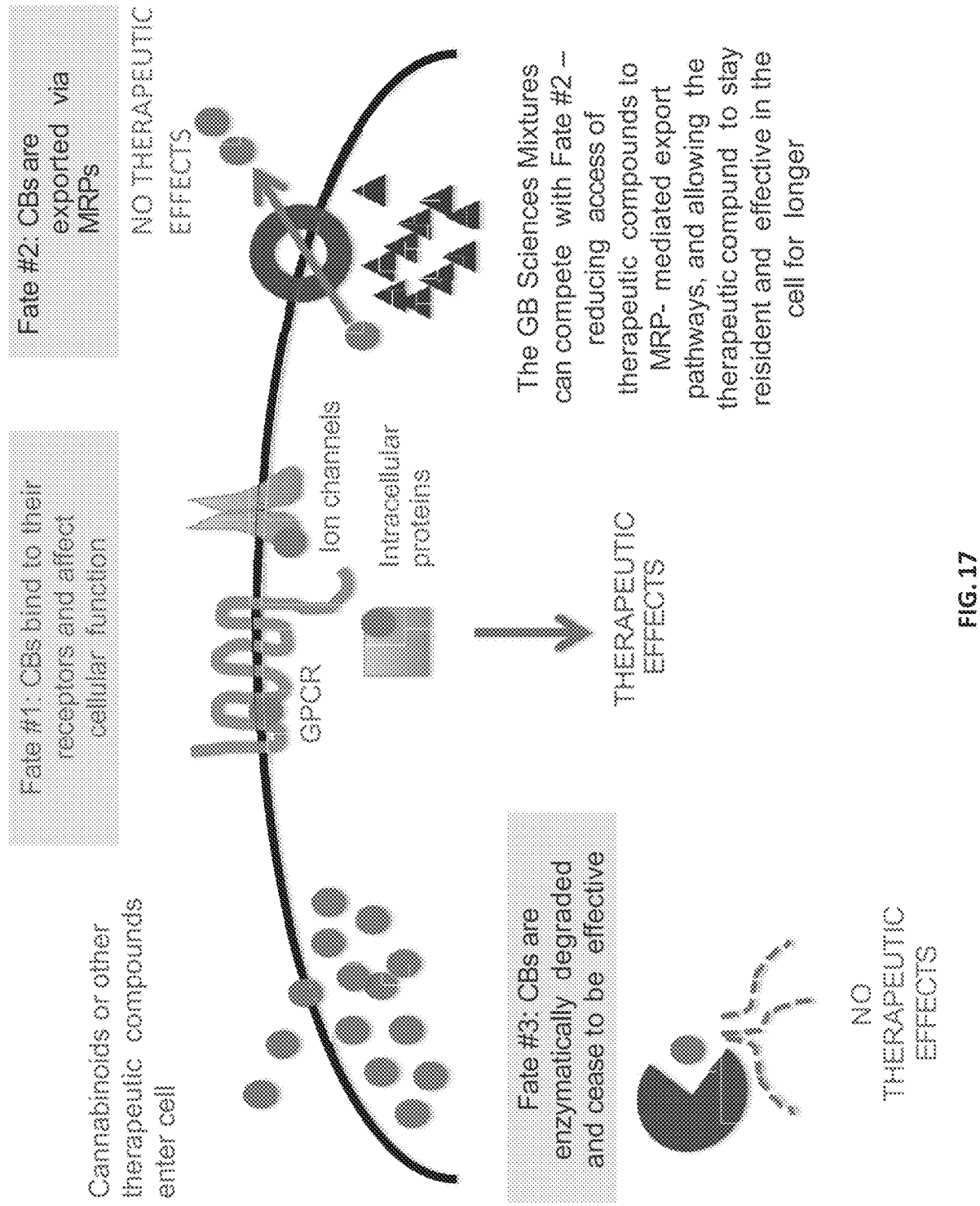

FIG. 17 illustrates one mechanism by which the cannabinoids and terpenes other than myrcene in the Strain A Mixture enhance the TRPV1 agonist activity of myrcene, through blocking of multidrug resistance protein-mediated export of the bioactive ligand (see FIG. 10).

FIG. 18 illustrates the predicted potential of myrcene, and mixtures containing myrcene, to target multiple receptors in the nociceptive nerve bundle.

Figure 19A:
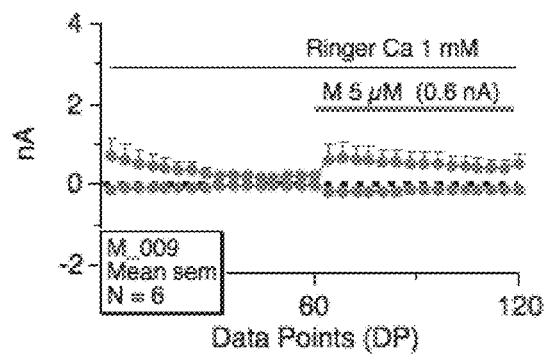
Figure 19B:
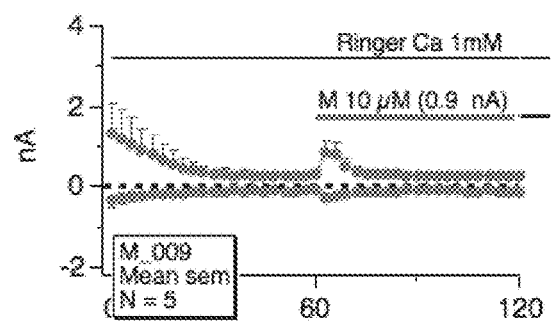
Figure 19C:
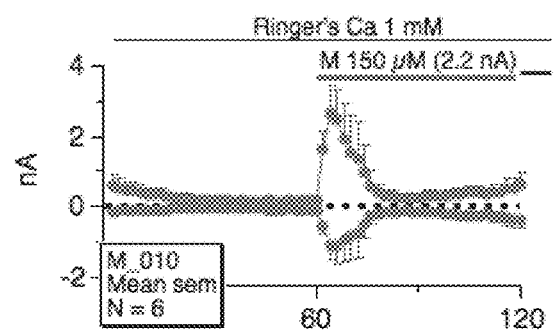

FIGS. 19A-19C illustrate TRPV1 ion channel activation in single HEK293 cells overexpressing TRPV1 after application of increasing amounts of myrcene (M). FIG. 19A shows 5 µM myrcene, FIG. 19B shows 10 µM myrcene, and FIG. 19C shows 150 µM myrcene.

Figure 20A:
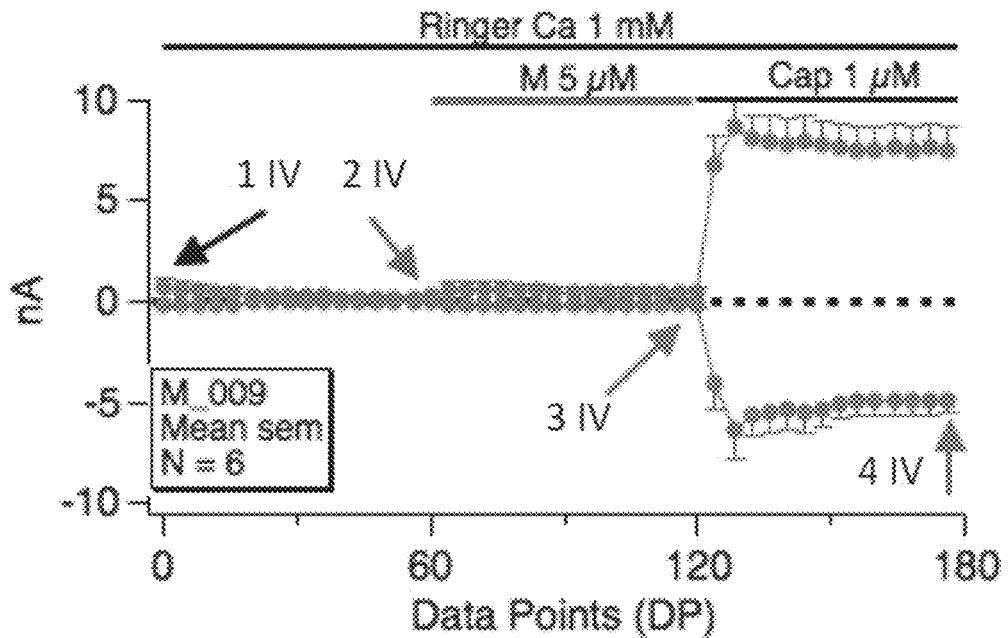
Figure 20B:
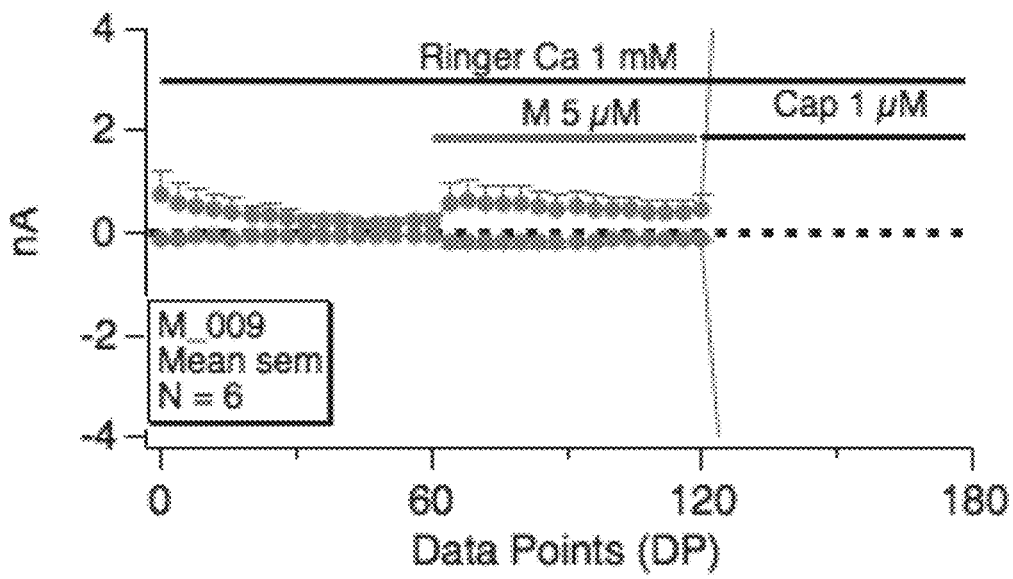
Figure 20C:
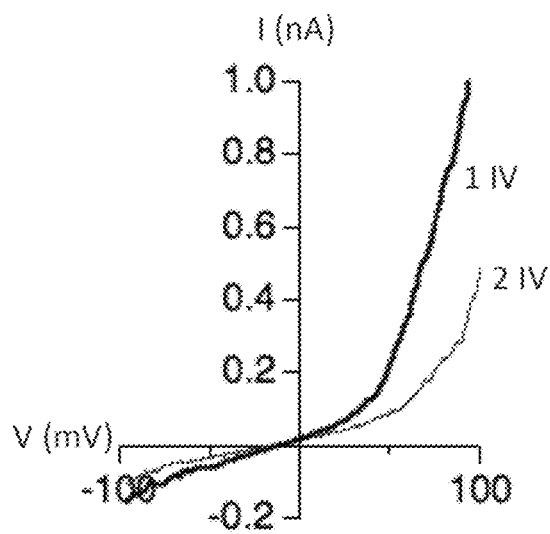
Figure 20D:
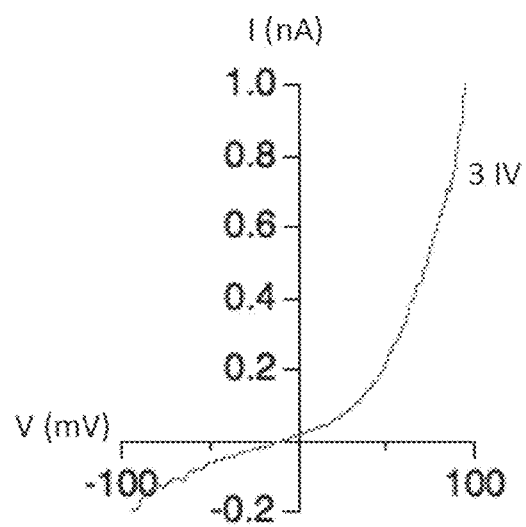
Figure 20E:
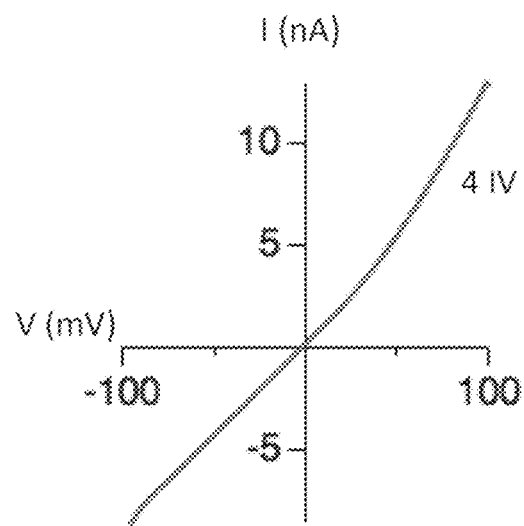

FIGS. 20A-20E illustrate electrophysiology data in single HEK293 cells overexpressing TRPV1 after addition of 5 µM myrcene (M) and 1 µM capsaicin (Cap). FIGS. 20A and 20B show the inward and outward ion current (nA) of the cell before and after myrcene and capsaicin addition. FIG. 20B is an enlarged view of FIG. 20A to show the myrcene-induced response. FIGS. 20C-20E show the current/voltage trace of the cell before myrcene or capsaicin is added (FIG. 20C), or after 5 µM myrcene (FIG. 20D) or 1 µM capsaicin (FIG. 20E).

4. DETAILED DESCRIPTION

4.1. Definitions

Unless defined otherwise, all technical and scientific terms used herein have the meaning commonly understood by a person skilled in the art to which this invention belongs. As used herein, the following terms have the meanings ascribed to them below.

"Myrcene" (synonymously "β-myrcene") is 7-methyl-3-methylideneocta-1,6-diene.

"Strain A Mixture" means a mixture of cannabidivarin (CBDV), cannabichromene (CBC), cannabidiol (CBD), cannabidiolic acid (CBDA), cannabigerol (CBG), cannabigerolic acid (CBGA), cannabinol (CBN), alpha-bisabolol (α-bisabolol), alpha-humulene (α-humulene), alpha-pinene (α-pinene), beta-caryophyllene (β-caryophyllene), myrcene, (+)-beta-pinene (β-pinene), camphene, limonene, linalool, and nerolidol. See Table 1 and FIG. 15. The composition of the mixture is based upon the actual chemo-profile of a *Cannabis sativa* cultivar currently used medicinally in Nevada, USA. Strain chemo-profile data was expressed as % mass and mg/g abundance, and these amounts were converted to amounts to be included in the mixture for exposure to cultured cells. The actual chemo-profile was modified in the Strain A Mixture by deliberate omission of THC and THCA, and omission of certain labile or insoluble components.

"Terpene Mixture" means a mixture containing only the terpenes of the Strain A Mixture—alpha-bisabolol (α-bisabolol), alpha-humulene (α-humulene), alpha-pinene (α-pinene), beta-caryophyllene (β-caryophyllene), myrcene, (+)-beta-pinene (β-pinene), camphene, limonene, linalool, and nerolidol.

"Selected Terpene" means nerolidol.

"Cannabinoid Mixture" means a mixture containing only the cannabinoids of the Strain A Mixture—cannabidivarin (CBDV), cannabichromene (CBC), cannabidiol (CBD), cannabidiolic acid (CBDA), cannabigerol (CBG), cannabigerolic acid (CBGA), and cannabinol (CBN).

"Selected Cannabinoid" means cannabigerolic acid (CBGA), cannabidiol (CBD), cannabidivarin (CBDV), cannabichromene, cannabidiolic acid, or cannabigerol (CBG).

"Pharmaceutically active ingredient" (synonymously, active pharmaceutical ingredient) means any substance or mixture of substances intended to be used in the manufacture of a drug product and that, when used in the production of a drug, becomes an active ingredient in the drug product. Such substances are intended to furnish pharmacological activity or other direct effect in the diagnosis, cure, mitigation, treatment or prevention of disease or to affect the structure and function of the body. Such substances or mixture of substances are preferably generated in compliance with the Current Good Manufacturing Practice (CGMP) regulations pursuant to Section 501(a)(2)(B) of the Federal Food, Drug, and Cosmetic Act.

A pharmaceutically active ingredient is "substantially free of THC" if the ingredient contains less than 0.3% (w/w) of delta-9 tetrahydrocannabinol. A pharmaceutical composition is "substantially free of THC" if the pharmaceutical composition contains less than 0.3% (w/v) of delta-9 tetrahydrocannabinol.

A "*Cannabis sativa* extract" is a composition obtained from *Cannabis sativa* plant materials by fluid and/or gas extraction, for example by supercritical fluid extraction (SFE) with $CO_2$. The *Cannabis sativa* extract typically contains myrcene, selected cannabinoids, selected terpenes, and also other terpenes, phytocannabinoids, and secondary metabolites. For example, the *Cannabis sativa* extract can include one or more of terpinene, caryophyllene, geraniol, guaiol, isopulegoll, ocimene, cymene, eucalyptol, and terpinolene.

"Pain disorders" include various diseases causing pain as one of their symptoms—including, but not limited to, those associated with strains, sprains, arthritis or other joint pain, bruising, backaches, fibromyalgia, endometriosis, pain after surgery, diabetic neuropathy, trigeminal neuralgia, postherpetic neuralgia, cluster headaches, psoriasis, irritable bowel syndrome, chronic interstitial cystitis, vulvodynia, trauma, musculoskeletal disorders, shingles, sickle cell disease, heart disease, cancer, stroke, or mouth sores due to chemotherapy or radiation.

The terms "treatment," "treating," and the like are used herein to generally mean obtaining a desired pharmacologic and/or physiologic effect. The effect may be prophylactic, in terms of completely or partially preventing a disease, condition, or symptoms thereof, and/or may be therapeutic in terms of a partial or complete cure for a disease or condition and/or adverse effect, such as a symptom, attributable to the disease or condition. "Treatment" as used herein covers any treatment of a disease or condition of a mammal, particularly a human, and includes: (a) preventing the disease or condition from occurring in a subject which may be predisposed to the disease or condition but has not yet been diagnosed as having it; (b) inhibiting the disease or condition (e.g., arresting its development); or (c) relieving the disease or condition (e.g., causing regression of the disease or condition, providing improvement in one or more symptoms). Improvements in any conditions can be readily assessed according to standard methods and techniques known in the art. The population of subjects treated by the method includes subjects suffering from the undesirable condition or disease, as well as subjects at risk for development of the condition or disease.

By the term "therapeutically effective dose" or "therapeutically effective amount" is meant a dose or amount that produces the desired effect for which it is administered. The exact dose or amount will depend on the purpose of the treatment, and will be ascertainable by one skilled in the art using known techniques (see, e.g., Lloyd (2012) The Art, Science and Technology of Pharmaceutical Compounding, Fourth Edition). A therapeutically effective amount can be a "prophylactically effective amount" as prophylaxis can be considered therapy.

The term "sufficient amount" means an amount sufficient to produce a desired effect.

The term "ameliorating" refers to any therapeutically beneficial result in the treatment of a disease state, e.g., an immune disorder, including prophylaxis, lessening in the severity or progression, remission, or cure thereof.

4.2. Other Interpretational Conventions

Ranges recited herein are understood to be shorthand for all of the values within the range, inclusive of the recited endpoints. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50.

Unless otherwise indicated, reference to a compound that has one or more stereo centers intends each stereoisomer, and all combinations of stereoisomers, thereof.

4.3. Overview of Experimental Results

*Cannabis* has been used for millennia to provide analgesia and treat various types of pain. We sought to determine whether *Cannabis* exerts its anti-nociceptive effects at least in part through the TRPV1 receptor, and if so, to determine which of the hundreds of compounds in a medicinal *Cannabis* extract contribute to the effect.

As described more fully in the Example section below, we prepared a complex mixture of cannabinoids and terpenes, the Strain A Mixture, based upon the actual chemo-profile of a *Cannabis sativa* cultivar currently used medicinally in Nevada, USA. Strain chemo-profile data was expressed as % mass and mg/g abundance, and these amounts were converted to amounts to be included in the mixture. The actual chemo-profile was modified in the Strain A Mixture by deliberate omission of THC and THCA, to eliminate psychoactive components, and omission of certain labile or insoluble components. We also prepared complex mixtures containing subsets of the compounds in the Strain A Mixture: CBMIX, Cannabinoid Mixture and Terpene Mixture. See Table 1.

Figure 1:
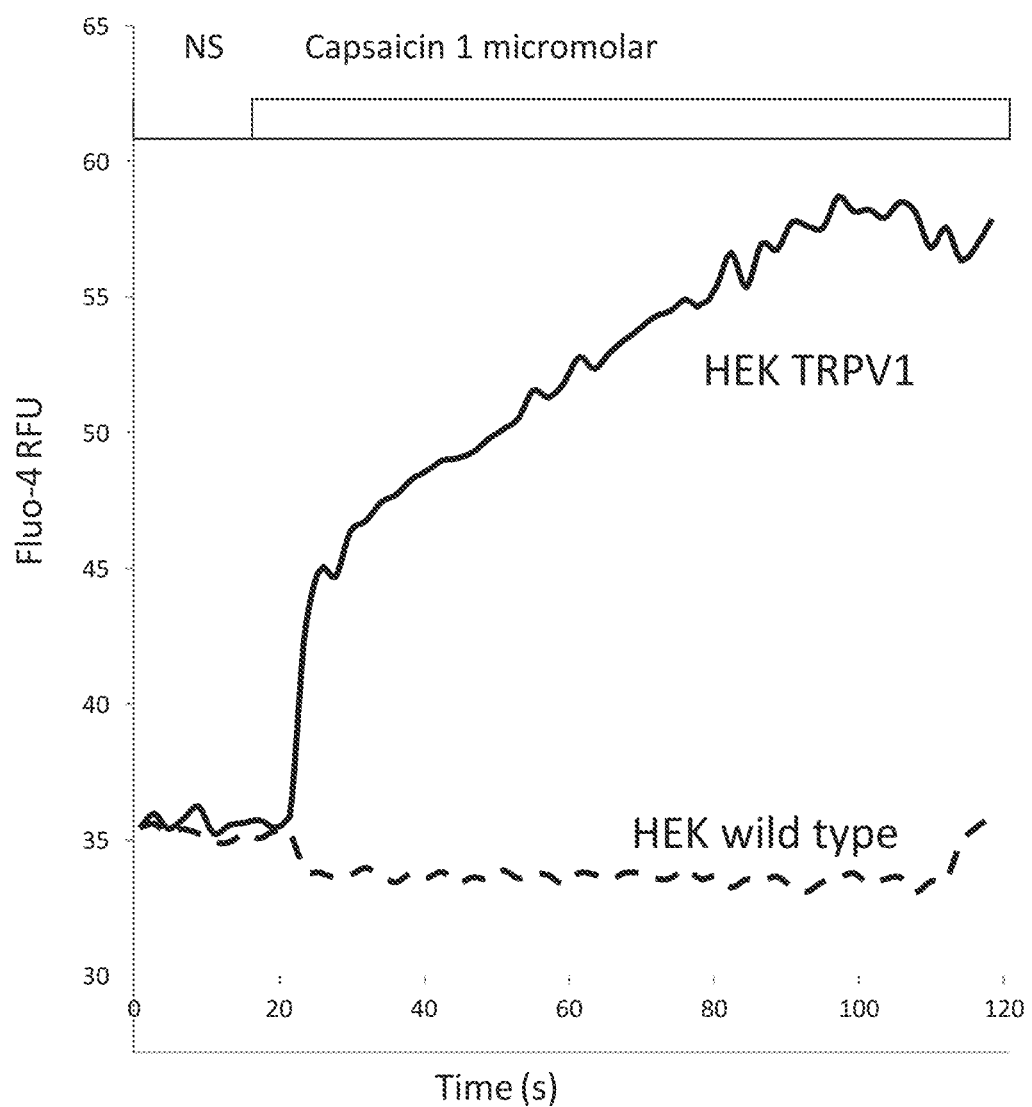

To create an in vitro assay for TRPV-1 agonist activity, we transfected HEK cells with an expression vector that confers tetracycline-inducible expression of TRPV1 on the cells, and used a standard fluorescent reporter of intracellular calcium levels (fluo-4 acetoxymethyl ester) ("fluo-4"). FIG. 1 illustrates that the inducible expression of TRPV1 confers capsaicin-sensitive calcium flux responses upon HEK cells, establishing that the experimental system clearly reports TRPV1-specific calcium fluxes.

Figure 2A:
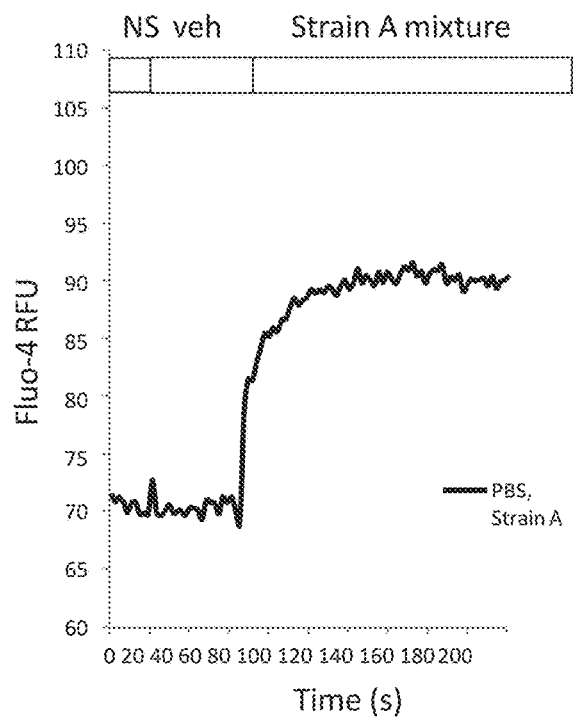
Figure 5A:
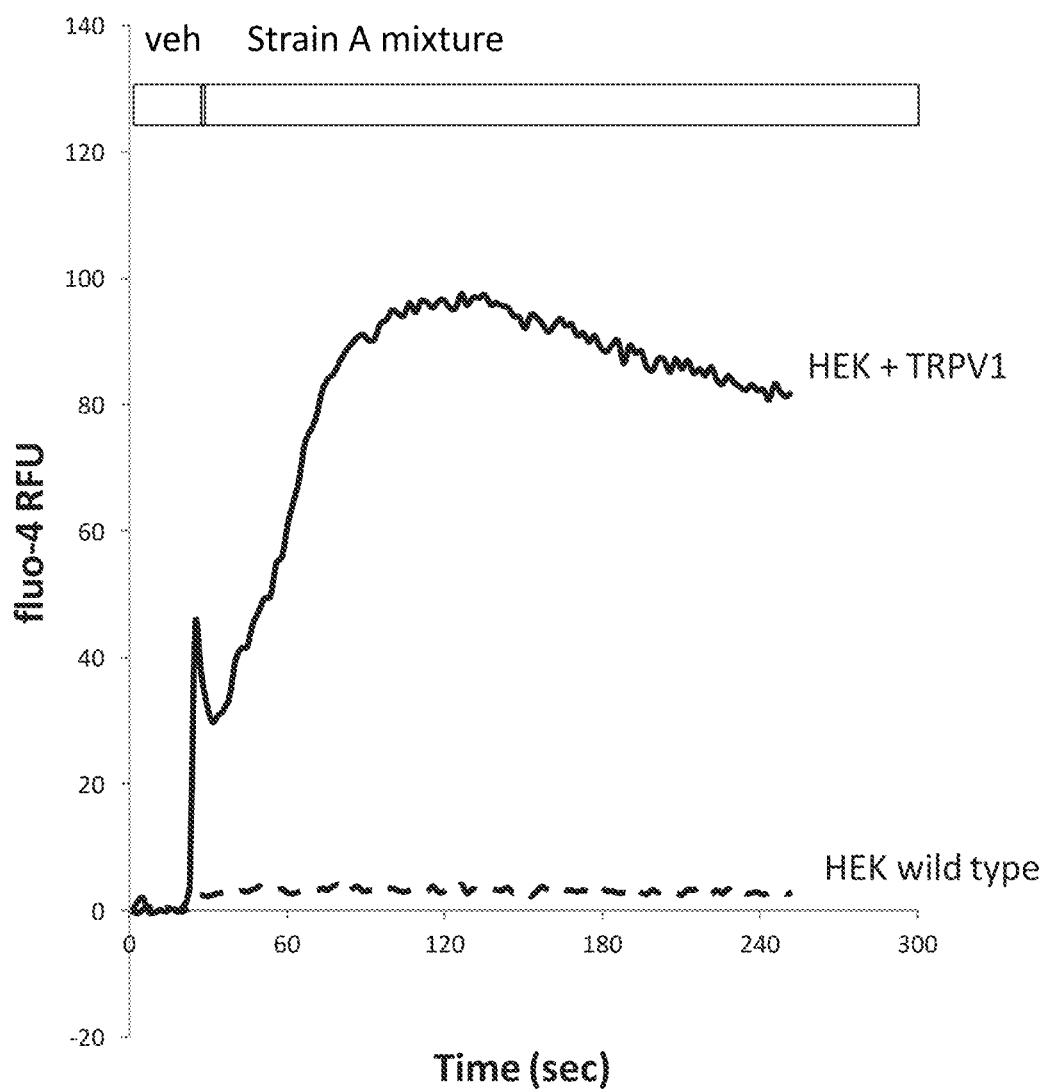

We tested the Strain A mixture in the same assay, and found that the *Cannabis*-derived mixture of cannabinoids and terpenes (Strain A mixture) causes significant calcium flux into the TRPV1-transfected HEK cells (FIG. 2A). We confirmed that the calcium fluxes observed with the complete Strain A mixture depends on the presence of the TRPV1 receptor by comparing signals obtained in parallel with untransfected wild type HEK cells (FIG. 5A).

Figure 2B:
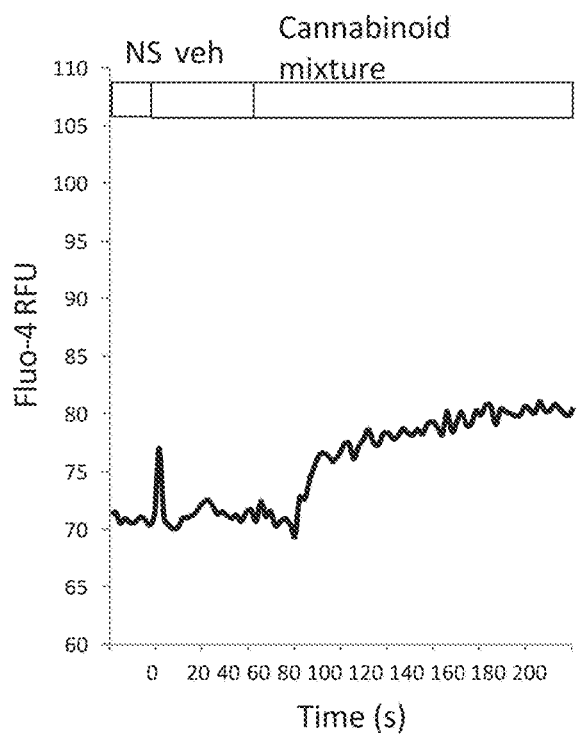
Figure 2C:
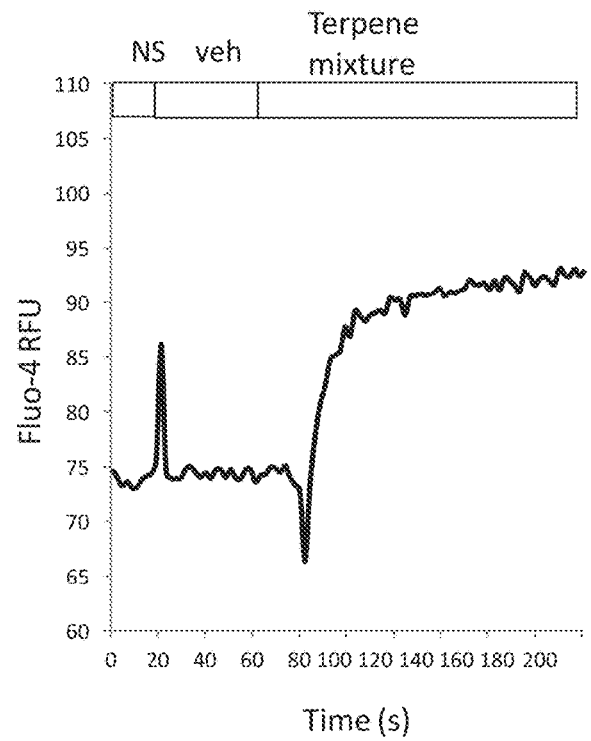
Figure 5B:
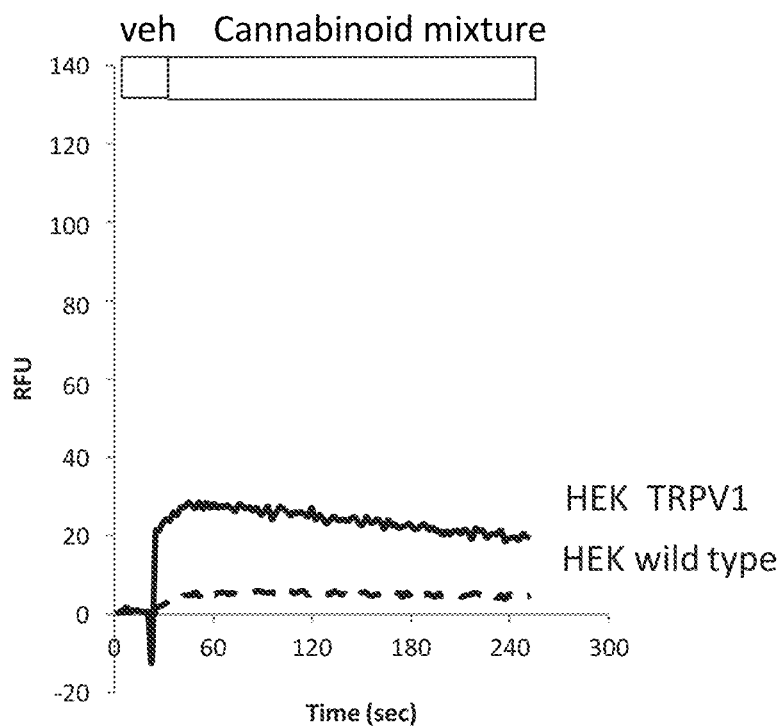
Figure 5C:
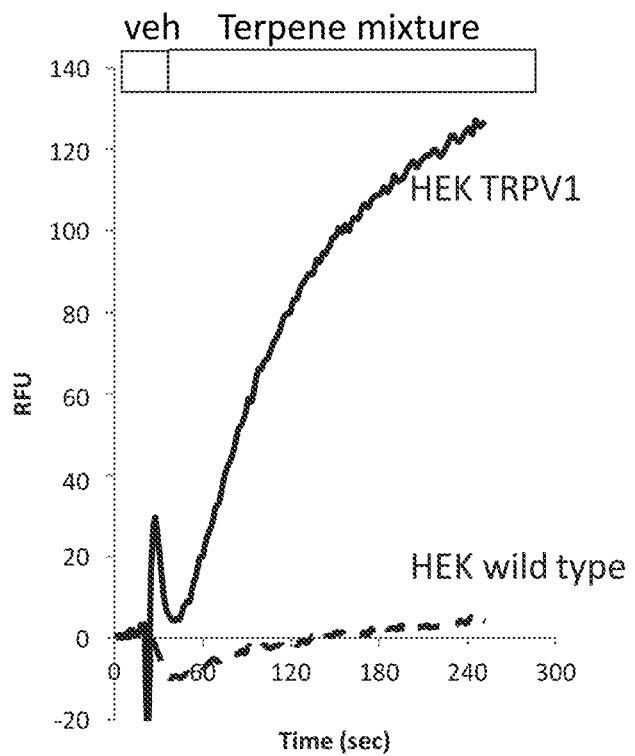
Figure 6A:
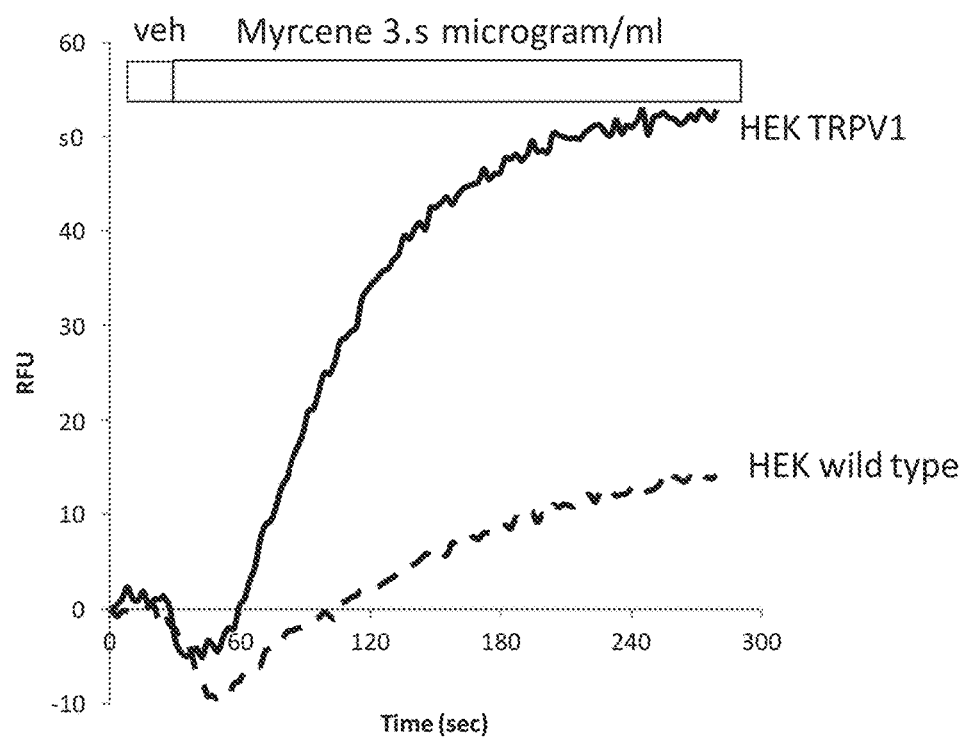
Figure 6B:
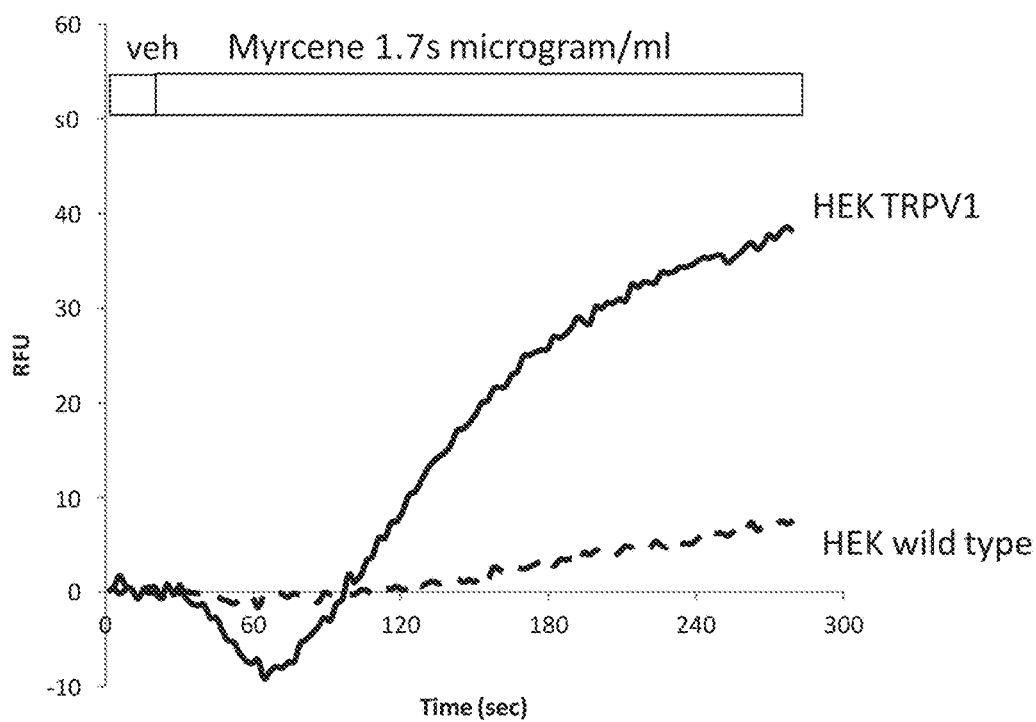
Figure 6C:
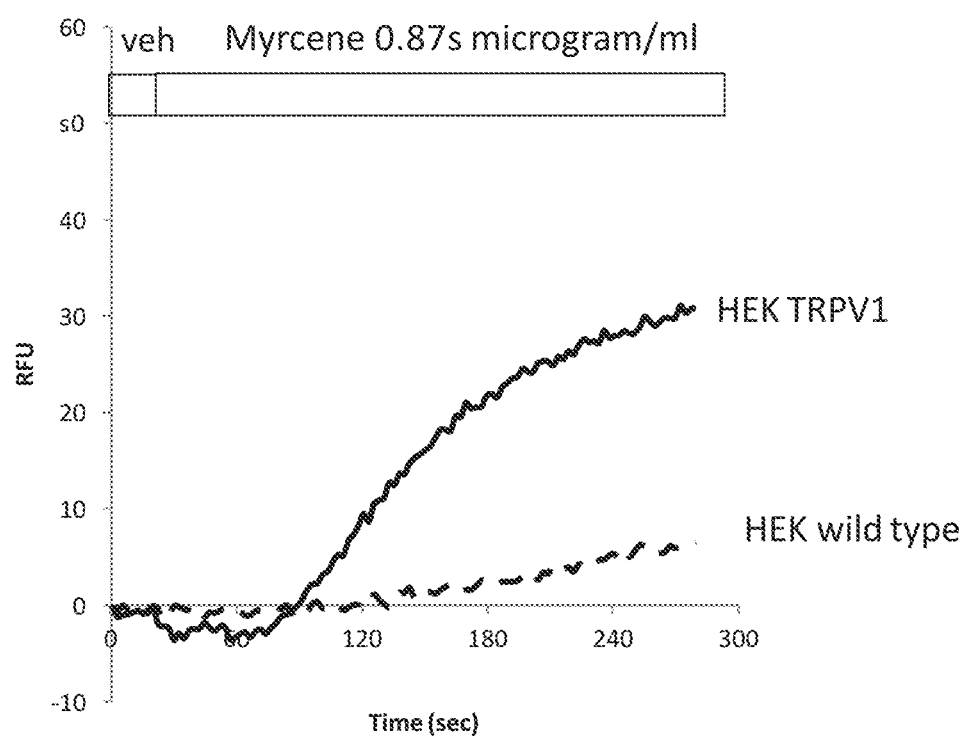
Figure 6D:
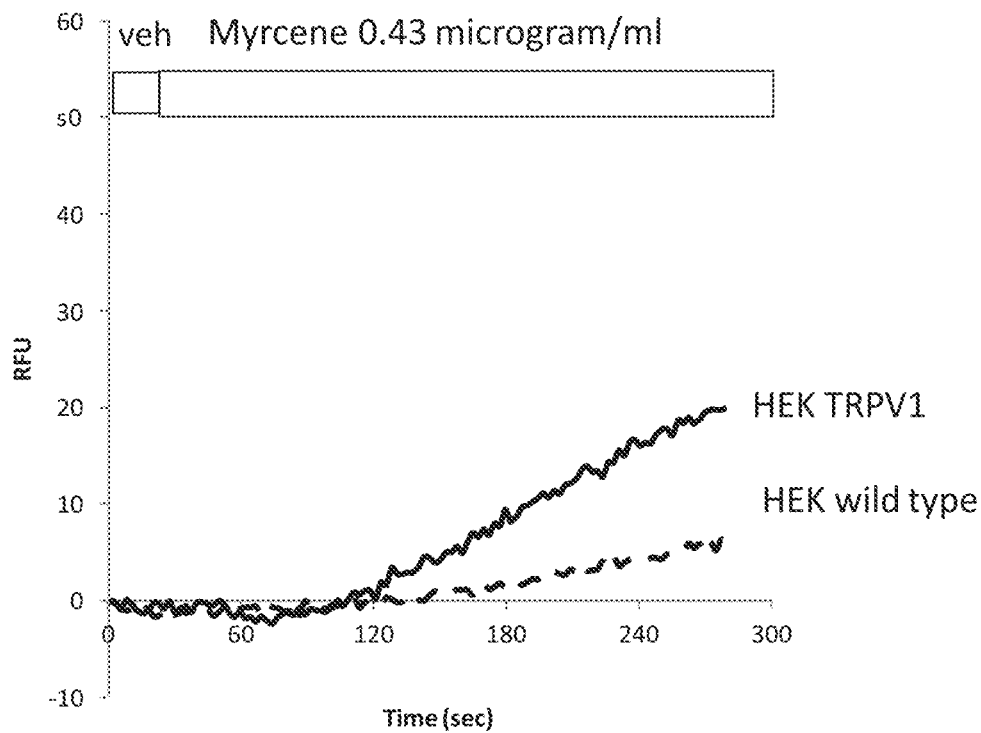

Using sub-mixtures, we determined that the terpenes in the Strain A mixture contribute significantly to the observed effect (FIG. 2C). More modest influx was caused by the cannabinoids present in the Strain A mixture (FIG. 2B). The signal observed using the Terpene Mixture and the Cannabinoid Mixture were dependent on the presence of the TRPV1 receptor (FIGS. 5B, 5C).

Figure 3A:
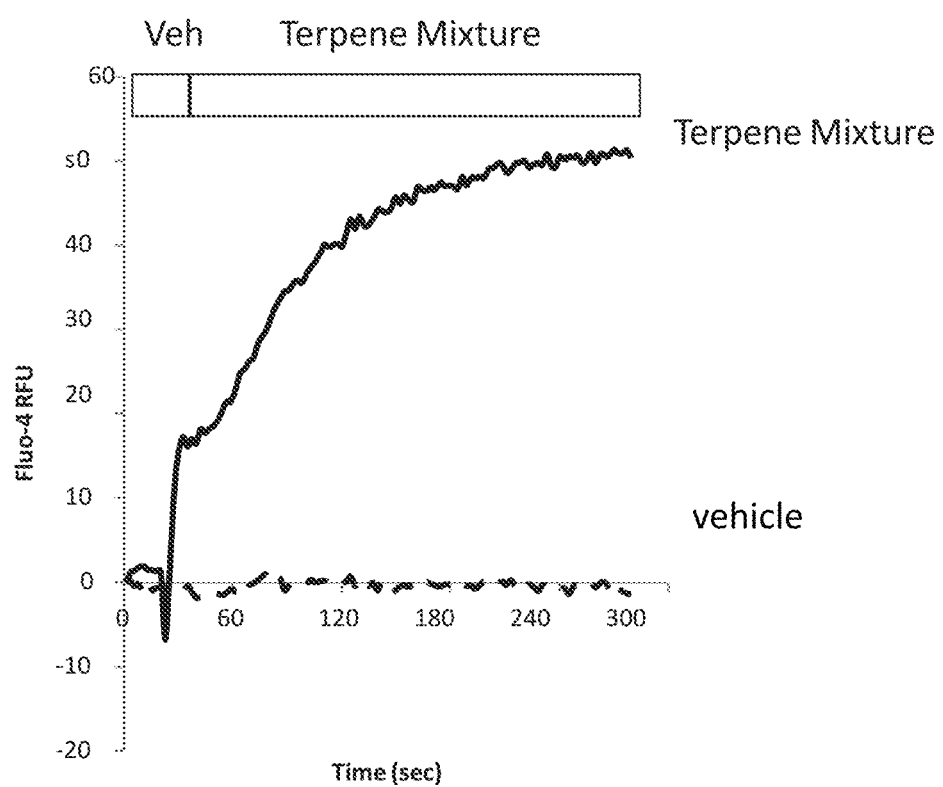
Figure 3B:
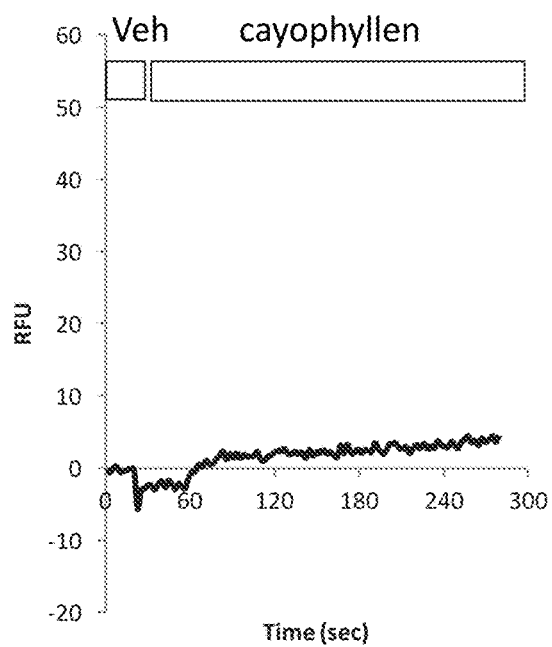
Figure 3C:
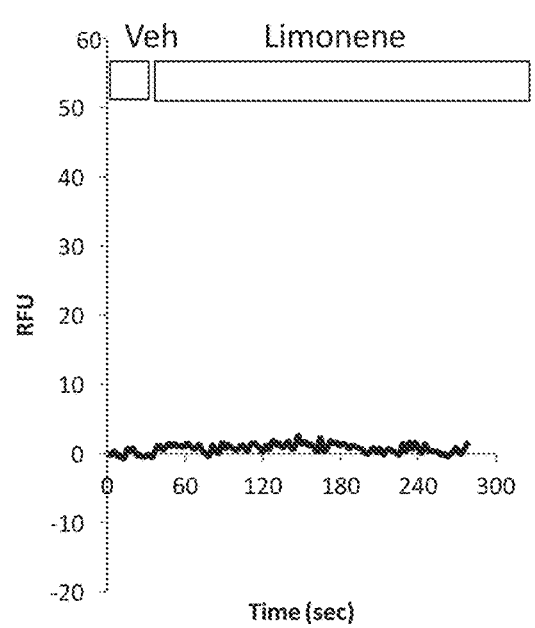
Figure 3D:
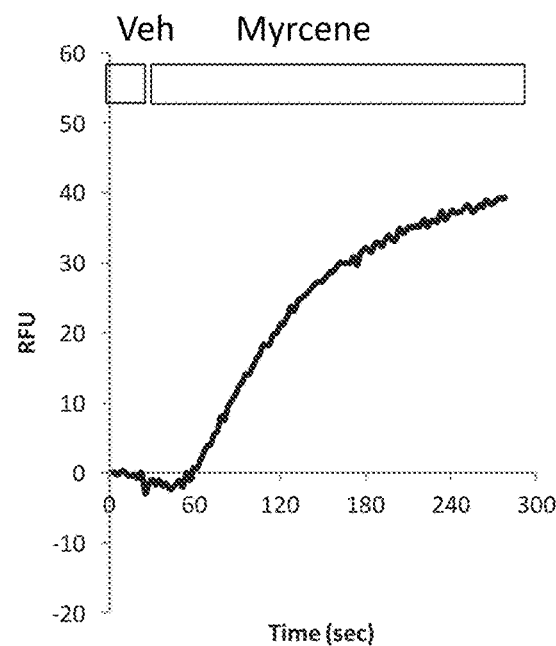
Figure 3E:
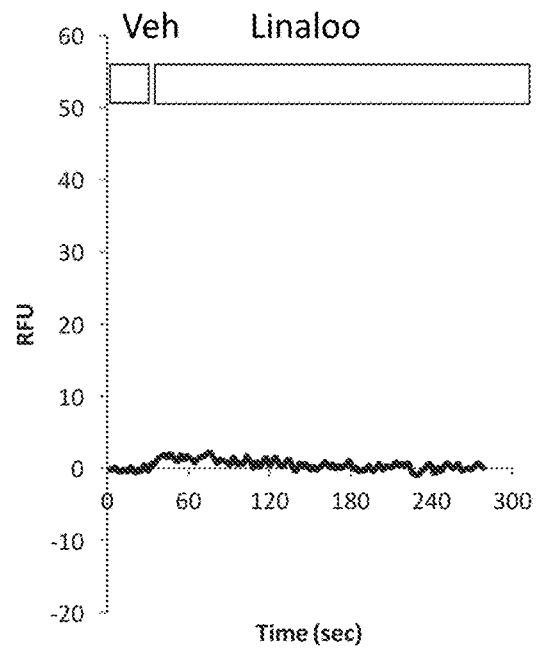
Figure 3F:
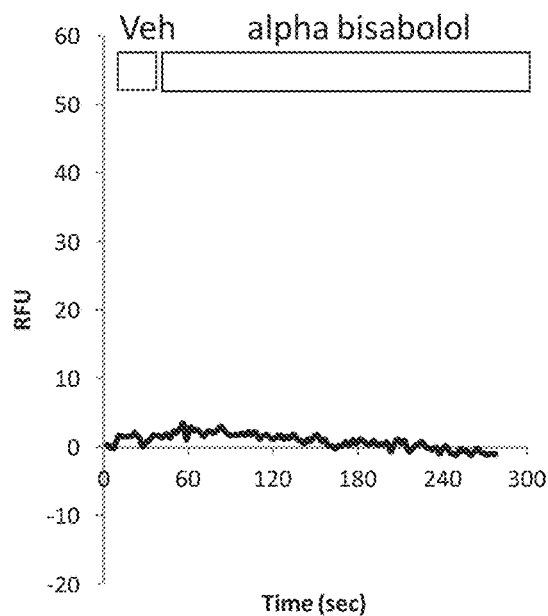
Figure 3G:
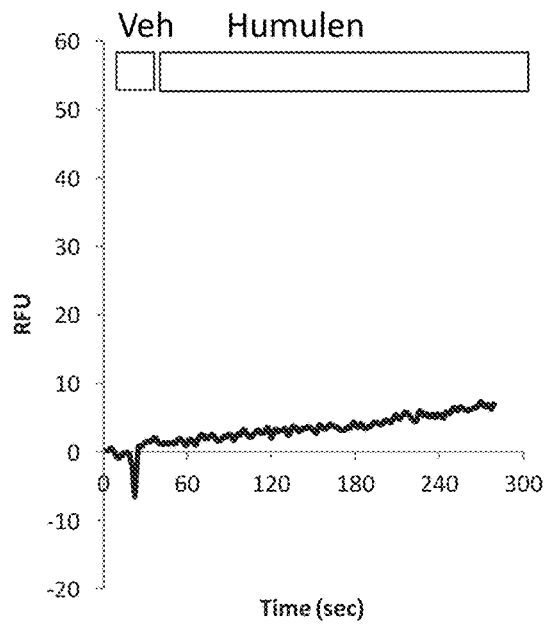
Figure 3H:
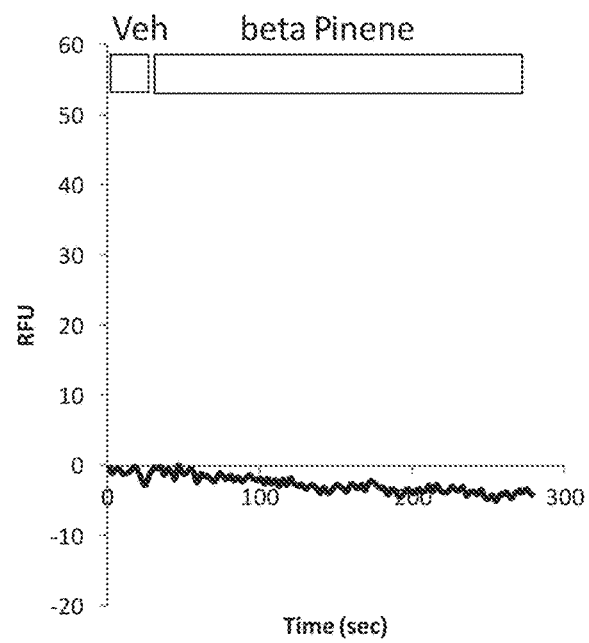
Figure 3I:
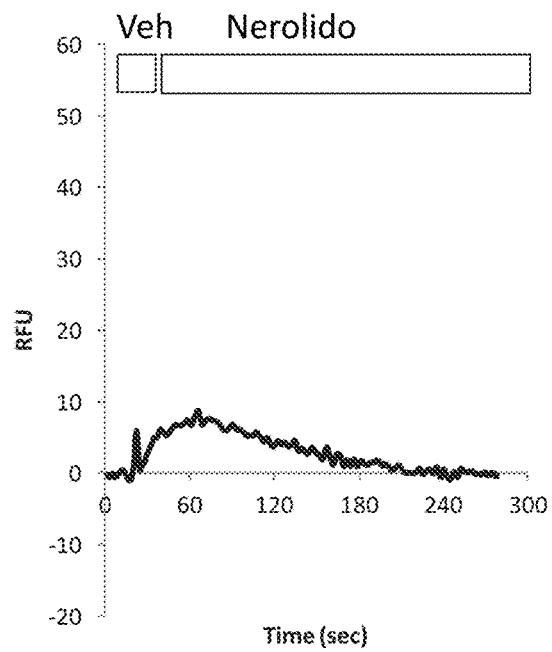
Figure 4:
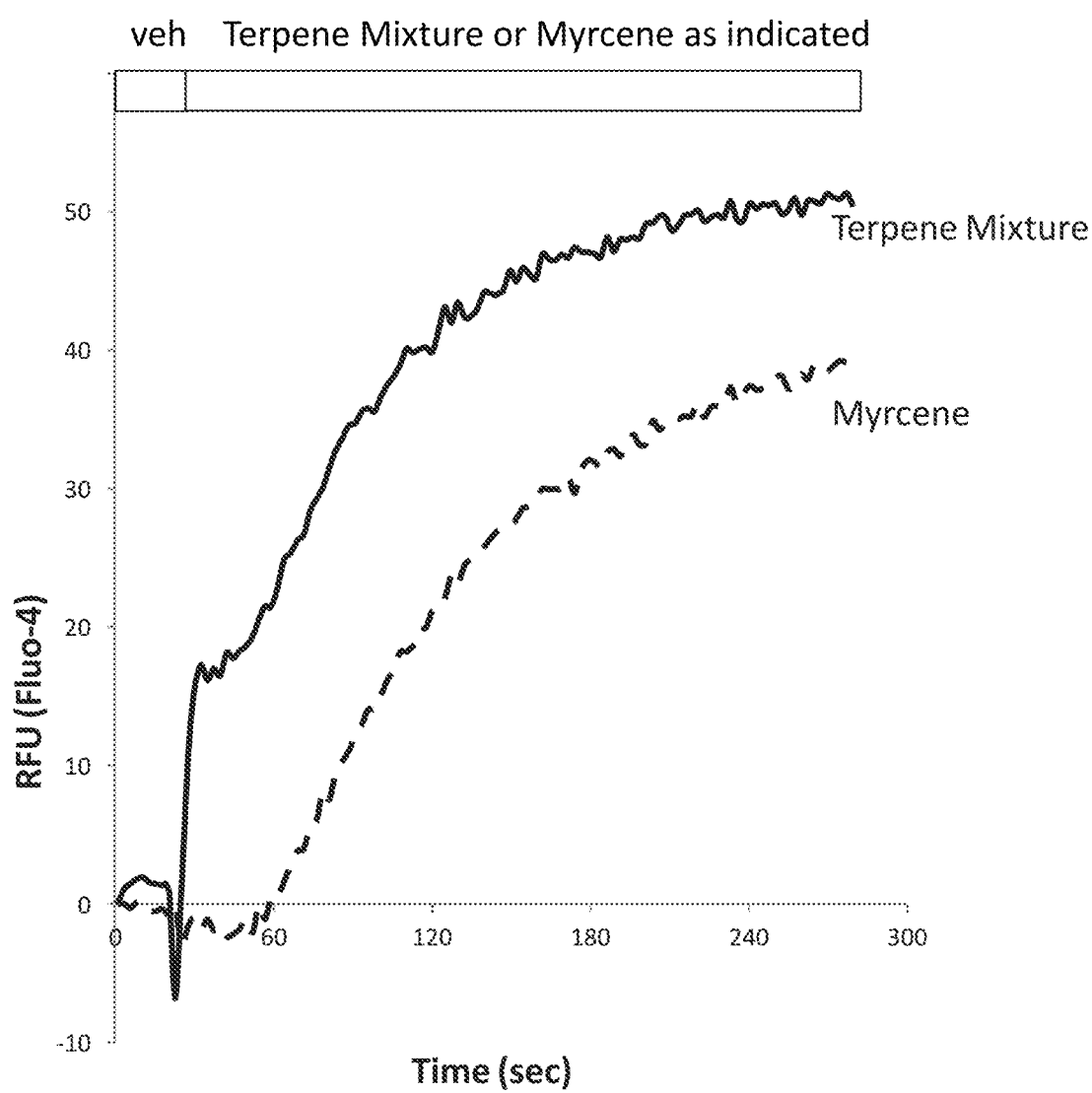

We then tested individual terpenes present in the Strain A mixture and found that individual terpenes differentially contribute to calcium fluxes via TRPV1 (FIGS. 3A-3L). Myrcene contributes significant agonist activity (FIG. 3C), but does not constitute 100% of the signal (FIG. 4). Nerolidol was observed to have more modest agonist activity when tested alone (FIG. 3I). The myrcene-induced influx of calcium was dose-dependent, and dependent wholly or in part on expression of TRPV1 receptors (FIG. 6). We further confirmed the dependence on TRPV1 using the TRPV1 inhibitor, capsazepine; FIG. 7 illustrates that the myrcene-induced calcium influx responses are inhibited by capsazepine.

We demonstrated that in the absence of extracellular calcium (achieved by construction of a nominally calcium-free extracellular milieu supplemented with 1 mM EGTA), at high concentrations myrcene can induce TRPV1-dependent calcium release from internal stores (FIG. 8).

We compared the acute agonist potency of myrcene to capsaicin and found that higher concentrations of myrcene were needed to induce the same calcium influx as capsaicin (FIG. 14A). The data suggest that myrcene is an effective TRPV1 agonist that works similarly to capsaicin, but with lower potency. And like capsaicin, myrcene causes desensitization after 24 hour exposure.

We performed similar experiments to determine the contribution of individual cannabinoids in the Strain A mixture, and found that that cannabinoids differentially contribute to calcium fluxes via TRPV1 (FIGS. 9A-9G). Of the cannabinoids, cannabigerolic acid (CBGA), cannabidiol (CBD), cannabidivarin (CBDV), cannabichromene, and cannabidiolic acid were most potent when tested individually in the assay, To explore the mechanism by which the complex mixture of terpenes and cannabinoids in the Strain A mixture provides a higher signal than myrcene alone, we tested whether the *Cannabis*-like 'entourage' might be acting to block the multidrug resistance protein-mediated export of the bioactive ligand, myrcene. Multi-drug Resistance Protein (MRP)-mediated efflux rates of the fluorescent marker CFDA were evaluated by flow cytometry in the presence of vehicle only ("veh"), the known MRP inhibitor, chloroquine ("Chloroquine"), and in the presence of "CBMIX", a mixture of all of the cannabinoids and terpenes in the Strain A Mixture other than myrcene. The data, shown in FIG. 10, suggest that if used as an adjunct to a primary therapeutic compound, co-application of a plurality of cannabinoids and/or terpenes would tend to delay the efflux of the therapeutic compound from the cell and thus increase the specific activity of the primary therapeutic compound per unit dose.

In order to assess the broader therapeutic potential of myrcene and nerolidol, the two terpenes in our original Cannabis Strain A Mixture with significant TRPV1 agonist effects, we used a proprietary in silico prediction approach, termed the GB Sciences' Network Pharmacology Platform ("NPP").

FIG. 11 illustrates that Therapeutic Target Database enrichment analysis tends to prioritize myrcene over nerolidol for development in pain and cardiovascular areas. In addition, myrcene contributes significantly to the predicted disease target set for native Cannabis. FIG. 12 illustrates that diverse ion channel targets are predicted for direct or indirect modulation by myrcene, whereas FIG. 13 illustrates that a more limited set of ion channel targets or CNS-active targets are predicted for direct or indirect modulation by nerolidol FIG. 16 A shows a target analysis and disease-prediction network for myrcene using GB Sciences' NPP. The presence of multiple TRP channels in the network indicates that efficacy of myrcene will likely extend beyond TRPV1 to other nociceptive neurons in which the primary pain conduction channel is a distinct TRP receptor.

4.4. Pharmaceutical Compositions

Accordingly, in a first aspect, pharmaceutical compositions are provided. The composition comprises myrcene and a pharmaceutically acceptable carrier or diluent. The composition optionally comprises at least one cannabinoid and/or at least one terpene other than myrcene. The composition comprises no more than 20 different species of cannabinoid and terpene compounds, and in typical embodiments is substantially free of THC.

In various embodiments, the pharmaceutical composition comprises no more than 19 different species of cannabinoid and terpene compounds, 18 different species, 17 different species, 16 different species, 15 different species, 14 different species, 13 different species, 12 different species, 11 different species, or no more than 10 different species. In certain embodiments, the pharmaceutical composition comprises no more than 9 different species of cannabinoid and terpene compounds, no more than 8 different species, no more than 7 different species, no more than 6 different species, or no more than 5 different species. In particular embodiments, the pharmaceutical composition comprises no more than 4 different species of cannabinoid and terpene compounds, no more than 3 different species, or no more than 2 different species. In a select embodiment, the pharmaceutical composition comprises no more than 1 species of cannabinoid and terpene compounds, which species is myrcene.

In various embodiments, the pharmaceutical composition comprises at least 2 different species of cannabinoid and terpene compounds, at least 3 different species, at least 4 different species, at least 5 different species, at least 6 different species, at least 7 different species, at least 8 different species, at least 9 different species, or at least 10 different species, in each case comprising no more than 20 different species. In some embodiments, the pharmaceutical composition comprises at least 11 different species of cannabinoid and terpene compounds, at least 12 different species, at least 13 different species, at least 14 different species, or at least 15 different species, in each case comprising no more than 20 different species.

In some embodiments, the pharmaceutical composition comprises 20 different species of cannabinoid and terpene compounds, 19 different species, 18 different species, 17 different species, 16 different species, 15 different species, 14 different species, 13 different species, 12 different species, 11 different species, or 10 different species. In various embodiments, the pharmaceutical composition comprises 9, 8, 7, 6, 5, 4, 3, or 2 different species of cannabinoid and terpene compounds.

In various embodiments, myrcene is present in an amount that is at least 10% (w/w) of the total content of cannabinoids and terpenes in the pharmaceutical composition. In some embodiments, myrcene is present in an amount that is at least 15% (w/w), at least 20% (w/w), at least 25% (w/w), at least 30% (w/w), at least 35% (w/w), at least 40% (w/w), at least 45% (w/w), or at least 50% (w/w) of the total content of cannabinoids and terpenes in the pharmaceutical composition. In certain embodiments, myrcene is present in an amount that is at least 55% (w/w), at least 60% (w/w), at least 65% (w/w), at least 70% (w/w), at least 75% (w/w), at least 80% (w/w), at least 85% (w/w), or at least 90% (w/w) of the total content of cannabinoids and terpenes in the pharmaceutical composition. In particular embodiments, myrcene is present in an amount that is at least 95% (w/w) of the total content of cannabinoids and terpenes in the pharmaceutical composition.

In various embodiments, myrcene is present in the pharmaceutical composition at a concentration of 0.025%-5% (w/v). In some embodiments, myrcene is present in the pharmaceutical composition at a concentration of 0.025%-2.5% (w/v). In some embodiments, myrcene is present in the pharmaceutical composition at a concentration of 0.025%-1% (w/v). In some embodiments, myrcene is present in the pharmaceutical composition at a concentration of 2% (w/v), 3% (w/v), 4% (w/v), 5% (w/v), 6% (w/v), 7% (w/v), 8% (w/v), 9% (w/v), or 10% (w/v).

In some embodiments comprising at least two different species of cannabinoid and terpene compounds, at least one of the compounds other than myrcene is a Selected Cannabinoid. In certain embodiments comprising at least two different species of cannabinoid and terpene compounds, all of the compounds other than myrcene are Selected Cannabinoids.

In various embodiments, the pharmaceutical composition comprises cannabigerolic acid (CBGA). In some embodiments, CBGA is present in an amount that is at least 10% (w/w) of the total content of cannabinoids and terpenes in the pharmaceutical composition. In some embodiments, CBGA is present in an amount that is at least 11% (w/w), 12% (w/w), 13% (w/w), 14% (w/w) or 15% (w/w) of the total content of cannabinoids and terpenes in the pharmaceutical composition. In some embodiments, CBGA is present in an amount that is at least 20% (w/w), 21% (w/w), 22% (w/w), 23% (w/w), 24% (w/w) or 25% (w/w) of the total content of cannabinoids and terpenes in the pharmaceutical composition.

In various embodiments, the pharmaceutical composition comprises cannabidiol (CBD). In some embodiments, CBD is present in an amount that is at least 2.5% (w/w) of the total content of cannabinoids and terpenes in the pharmaceutical composition. In some embodiments, CBD is present in an amount that is at least 3% (w/w), 3.5% (w/w), 4% (w/w), 4.5% (w/w) or 5% (w/w) of the total content of cannabinoids and terpenes in the pharmaceutical composition. In certain embodiments, CBD is present in an amount that is at least 7.5% (w/w) or 10% (w/w) of the total content of cannabinoids and terpenes in the pharmaceutical composition.

In various embodiments, the pharmaceutical composition comprises cannabidivarin (CBDV). In some embodiments, CBDV is present in an amount that is at least 5% (w/w) of the total content of cannabinoids and terpenes in the pharmaceutical composition. In some embodiments, CBDV is present in an amount that is at least 7.5% (w/w), 10% (w/w), or 15% (w/w) of the total content of cannabinoids and terpenes in the pharmaceutical composition.

In various embodiments, the pharmaceutical composition comprises cannabichromene. In some embodiments, cannabichromene is present in an amount that is at least 1% (w/w) of the total content of cannabinoids and terpenes in the pharmaceutical composition. In some embodiments, cannabichromene is present in an amount that is at least 1.5% (w/w), at least 2% (w/w), or at least 2.5% (w/w) of the total content of cannabinoids and terpenes in the pharmaceutical composition. In some embodiments, cannabichromene is present in an amount that is at least 5% (w/w), 7.5% (w/w) or 10% (w/w) of the total content of cannabinoids and terpenes in the pharmaceutical composition.

In various embodiments, the pharmaceutical composition comprises cannabidiolic acid (CBDA). In some embodiments, CBDA is present in an amount that is at least 2.5% (w/w) of the total content of cannabinoids and terpenes in the pharmaceutical composition. In some embodiments, CBDA is present in an amount that is at least 5% (w/w), 7.5% (w/w), or 10% (w/w) of the total content of cannabinoids and terpenes in the pharmaceutical composition.

In various embodiments, the composition comprises cannabigerol (CBG). In some embodiments, CBG is present in an amount that is at least 2.5% (w/w) of the total content of cannabinoids and terpenes in the pharmaceutical composition. In some embodiments, CBG is present in an amount that is at least 5% (w/w) of the total content of cannabinoids and terpenes in the pharmaceutical composition.

In some embodiments comprising at least two different species of cannabinoid and terpene compounds, at least one of the compounds other than myrcene is a Selected Terpene. In certain embodiments comprising at least two different species of cannabinoid and terpene compounds, all of the compounds other than myrcene are Selected Terpenes.

In various embodiments, the pharmaceutical composition comprises nerolidol. In some embodiments, nerolidol is present in an amount that is at least 2% (w/w) of the total content of cannabinoids and terpenes in the pharmaceutical composition. In some embodiments, nerolidol is present in an amount that is at least 2.5% (w/w), 3% (w/w), 3.5% (w/w), 4% (w/w), 4.5% (w/w) or 5% (w/w) of the total content of cannabinoids and terpenes in the pharmaceutical composition. In particular embodiments, nerolidol is present in an amount that is at least 7.5% (w/w) or 10% (w/w) of the total content of cannabinoids and terpenes in the pharmaceutical composition.

In typical embodiments, the cannabinoid and terpene compounds other than myrcene are present in amounts that are effective to increase myrcene-dependent TRPV1 calcium flux.

4.4.1. Delta-9 Tetrahydrocannabinol (THC) Content

In typical embodiments, the pharmaceutical composition is either completely or substantially free of delta-9 tetrahydrocannabinol (THC), and thus lacks psychoactive effects, which offers certain regulatory and other physiological advantages.

In certain embodiments, the pharmaceutical composition is not substantially free of delta-9 THC. In certain of these embodiments, the pharmaceutical composition comprises 1-10 percent by weight (wt %) THC. In specific embodiments, the pharmaceutical composition comprises 2-9 wt % THC, 3-8 wt % THC, 4-7 wt % THC. In certain embodiments, the pharmaceutical composition comprises 1, 2, 3, 4, 5, 6, 7, 8, 9 or 10 wt % THC.

4.4.2. Other Components

In some embodiments, myrcene, optional cannabinoids, and optional terpenes other than myrcene collectively constitute less than 100% by weight (wt %) of the active pharmaceutical ingredient in the pharmaceutical composition.

In various such embodiments, myrcene, optional cannabinoids, and optional terpenes other than myrcene collectively constitute at least 75% by weight, but less than 100 wt %, of the pharmaceutically active ingredient. In specific embodiments, myrcene, optional cannabinoids, and optional terpenes other than myrcene collectively constitute at least 80%, at least at least 85%, at least 90%, at least 91%, at least 92%, at least 93%, at least 94%, or at least 95% by weight, but less than 100 wt %, of the active ingredient. In particular embodiments, myrcene, optional cannabinoids, and optional terpenes other than myrcene collectively constitute at least 96%, at least 97%, at least 98%, or at least 99% by weight, but less than 100 wt %, of the active ingredient.

In embodiments in which myrcene, optional cannabinoids, and optional terpenes other than myrcene collectively constitute less than 100% by weight (wt %) of the pharmaceutically active ingredient, the active ingredient further comprises compounds other than myrcene, optional cannabinoids, and optional terpenes other than myrcene. In typical such embodiments, all other compounds in the active ingredient are extractable from *Cannabis sativa*. In specific embodiments, all other compounds in the active ingredient are present in an extract made from *Cannabis sativa*.

In some embodiments, myrcene, optional cannabinoids, and optional terpenes other than myrcene collectively constitute less than 100% (w/v) of the pharmaceutically active ingredient.

4.4.3. Formulation

The pharmaceutical composition can be in any form appropriate for administration to humans or non-human animals, including a liquid, an oil, an emulsion, a gel, a colloid, an aerosol, or a solid, and can be formulated for administration by any route of administration appropriate for human or veterinary medicine, including enteral and parenteral routes of administration.

4.4.3.1. Pharmacological Compositions Adapted for Administration by Inhalation In various embodiments, the pharmaceutical composition is formulated for administration by inhalation.

In certain embodiments, the pharmaceutical composition is formulated for administration by a vaporizer. In certain embodiments, the pharmaceutical composition is formulated for administration by a nebulizer. In particular embodiments, the nebulizer is a jet nebulizer or an ultrasonic nebulizer. In certain embodiments, the pharmaceutical composition is formulated for administration by an aerosolizer. In certain embodiments, the pharmaceutical composition is formulated for administration by dry powder inhaler.

In some embodiments, unit dosage forms of the pharmaceutical composition described herein are provided that are adapted for administration of the pharmaceutical composition by vaporizer, nebulizer, aerosolizer, or dry powder inhaler. In some embodiments, the dosage form is a vial, an ampule, optionally scored to allow user opening In various embodiments, the pharmaceutical composition is an aqueous solution, and can be administered as a nasal or pulmonary spray. Preferred systems for dispensing liquids as a nasal spray are disclosed in U.S. Pat. No. 4,511,069. Such formulations may be conveniently prepared by dissolving compositions according to the present invention in water to produce an aqueous solution, and rendering the solution sterile. The formulations may be presented in multi-dose containers, for example in the sealed dispensing system disclosed in U.S. Pat. No. 4,511,069. Other suitable nasal spray delivery systems have been described in Transdermal Systemic Medication, Y. W. Chien Ed., Elsevier Publishers, New York, 1985; M. Naef et al. Development and pharmacokinetic characterization of pulmonal and intravenous delta-9-tetrahydrocannabinol (THC) in humans, J. Pharm. Sci. 93, 1176-84 (2004); and in U.S. Pat. Nos. 4,778,810; 6,080,762; 7,052,678; and 8,277,781 (each incorporated herein by reference). Additional aerosol delivery forms may include, e.g., compressed air-, jet-, ultrasonic-, and piezoelectric nebulizers, which deliver the biologically active agent dissolved or suspended in a pharmaceutical solvent, e.g., water, ethanol, or a mixture thereof.

Mucosal formulations are, in certain embodiments, administered as dry powder formulations e.g., comprising the biologically active agent in a dry, usually lyophilized, form of an appropriate particle size, or within an appropriate particle size range, for intranasal delivery. Minimum particle size appropriate for deposition within the nasal or pulmonary passages is often about 0.5 micron mass median equivalent aerodynamic diameter (MMEAD), commonly about 1 micron MMEAD, and more typically about 2 micron MMEAD. Maximum particle size appropriate for deposition within the nasal passages is often about 10 micron MMEAD, commonly about 8 micron MMEAD, and more typically about 4 micron MMEAD. Intranasally respirable powders within these size ranges can be produced by a variety of conventional techniques, such as jet milling, spray drying, solvent precipitation, supercritical fluid condensation, and the like. These dry powders of appropriate MMEAD can be administered to a patient via a conventional dry powder inhaler (DPI) which rely on the patient's breath, upon pulmonary or nasal inhalation, to disperse the power into an aerosolized amount. Alternatively, the dry powder may be administered via air assisted devices that use an external power source to disperse the powder into an aerosolized amount, e.g., a piston pump.

4.4.3.2. Pharmacological Compositions Adapted for Oral/Buccal/Sublingual Administration In various embodiments, the pharmaceutical composition is formulated for oral, buccal, or sublingual administration.

Formulations for oral, buccal or sublingual administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a subject polypeptide therapeutic agent as an active ingredient. Suspensions, in addition to the active compounds, may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

In solid dosage forms for oral, buccal or sublingual administration (capsules, tablets, pills, dragees, powders, granules, and the like), one or more therapeutic agents may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like. Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

4.4.3.3. Pharmacological Compositions Adapted for Injection

In certain embodiments, the pharmaceutical composition is formulated for administration by injection.

For intravenous, intramuscular, or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives can be included, as required.

In various embodiments, the pharmaceutical composition is provided in a unit dosage form. The unit dosage form is a vial, ampule, bottle, or pre-filled syringe. In some embodiments, the unit dosage form contains 0.01 mg, 0.1 mg, 0.5 mg, 1 mg, 2.5 mg, 5 mg, 10 mg, 12.5 mg, 25 mg, 50 mg, 75 mg, or 100 mg of the cannabinoid composition. In some embodiments, the unit dosage form contains 125 mg, 150 mg, 175 mg, or 200 mg of the cannabinoid composition. In some embodiments, the unit dosage form contains 250 mg of the cannabinoid composition.

In typical embodiments, the pharmaceutical composition in the unit dosage form is in liquid form. In various embodiments, the unit dosage form contains between 0.1 mL and 50 ml of the pharmaceutical composition. In some embodiments, the unit dosage form contains 1 ml, 2.5 ml, 5 ml, 7.5 ml, 10 ml, 25 ml, or 50 ml of pharmaceutical composition.

In particular embodiments, the unit dosage form is a vial containing 1 ml of the myrcene-containing mixtures at a concentration of 0.01 mg/ml, 0.1 mg/ml, 0.5 mg/ml, or 1mg/ml. In some embodiments, the unit dosage form is a vial containing 2 ml of the myrcene-containing mixture at a concentration of 0.01 mg/ml, 0.1 mg/ml, 0.5 mg/ml, or 1 mg/ml.

In some embodiments, the pharmaceutical composition in the unit dosage form is in solid form, such as a lyophilate, suitable for solubilization.

Unit dosage form embodiments suitable for subcutaneous, intradermal, or intramuscular administration include pre-loaded syringes, auto-injectors, and autoinject pens, each containing a predetermined amount of the pharmaceutical composition described hereinabove.

In various embodiments, the unit dosage form is a pre-loaded syringe, comprising a syringe and a predetermined amount of the pharmaceutical composition. In certain pre-loaded syringe embodiments, the syringe is adapted for subcutaneous administration. In certain embodiments, the syringe is suitable for self-administration. In particular embodiments, the preloaded syringe is a single use syringe.

In various embodiments, the preloaded syringe contains about 0.1 mL to about 0.5 mL of the pharmaceutical composition. In certain embodiments, the syringe contains about 0.5 mL of the pharmaceutical composition. In specific embodiments, the syringe contains about 1.0 mL of the pharmaceutical composition. In particular embodiments, the syringe contains about 2.0 mL of the pharmaceutical composition.

In certain embodiments, the unit dosage form is an autoinject pen. The autoinject pen comprises an autoinject pen containing a pharmaceutical composition as described herein. In some embodiments, the autoinject pen delivers a predetermined volume of pharmaceutical composition. In other embodiments, the autoinject pen is configured to deliver a volume of pharmaceutical composition set by the user.

In various embodiments, the autoinject pen contains about 0.1 mL to about 5.0 mL of the pharmaceutical composition. In specific embodiments, the autoinject pen contains about 0.5 mL of the pharmaceutical composition. In particular embodiments, the autoinject pen contains about 1.0 mL of the pharmaceutical composition. In other embodiments, the autoinject pen contains about 5.0 mL of the pharmaceutical composition.

4.4.3.4. Pharmacological Compositions Adapted for Topical Administration

In various embodiments, the pharmaceutical formulation is formulated for topical administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Suitable topical formulations include those in which the myrcene-containing complex mixtures featured in the invention are in admixture with a topical delivery agent such as lipids, liposomes, fatty acids, fatty acid esters, steroids, chelating agents and surfactants. Suitable lipids and liposomes include neutral (e.g., dioleoylphosphatidyl DOPE ethanolamine, dimyristoylphosphatidyl choline DMPC, distearoylphosphatidyl choline) negative (e.g., dimyristoylphosphatidyl glycerol DMPG) and cationic (e.g., dioleoyltetramethylaminopropyl DOTAP and dioleoylphosphatidyl ethanolamine DOTMA). The myrcene-containing mixtures featured in the invention may be encapsulated within liposomes or may form complexes thereto, in particular to cationic liposomes. Alternatively, the myrcene-containing mixtures may be complexed to lipids, in particular to cationic lipids. Suitable fatty acids and esters include but are not limited to arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a C1-10 alkyl ester (e.g., isopropylmyristate IPM), monoglyceride, diglyceride or pharmaceutically acceptable salt thereof.

4.5. Process for Preparing Active Ingredient

In some embodiments, the pharmaceutically active ingredient is prepared by mixing chemically pure myrcene, optionally one or more selected cannabinoids, and optionally, a selected terpene, to desired final concentrations. Each of myrcene, selected cannabinoids, and selected terpenes can independently be chemically synthesized, either by total synthesis or by synthetic modification of an intermediate, purified from a compositional mixture such as a *Cannabis sativa* extract, or, as in the Examples described below, purchased commercially.

In other embodiments, the pharmaceutically active ingredient is prepared from a starting compositional mixture by adjusting to predetermined desired final concentrations any one or more of myrcene, optional selected cannabinoids, and optional selected terpenes. In typical embodiments, the starting compositional mixture is a *Cannabis sativa* extract. In currently preferred embodiments, the starting compositional mixture is a *Cannabis sativa* extract and one or more of the myrcene, selected cannabinoids, and selected terpenes is added to the mixture to achieve predetermined desired final concentrations.

Typically, in such embodiments, the process further comprises the earlier step of determining the concentration of each desired myrcene, optional selected cannabinoid, and optional selected terpene in the starting compositional mixture.

In certain of these embodiments, the process further comprises the still earlier step of preparing a *Cannabis sativa* extract. Methods of preparing *Cannabis sativa* extracts are described in U.S. Pat. Nos. 6,403,126, 8,895, 078, and 9,066,910; Doorenbos et al., Cultivation, extraction, and analysis of *Cannabis sativa* L., Annals of The New York Academy of Sciences, 191, 3-14 (1971); Fairbairn and Liebmann, The extraction and estimation of the cannabinoids in *Cannabis sativa* L. and its products, Journal of Pharmacy and Pharmacology, 25, 150-155 (1973); Oroszlan and Verzar-petri, Separation, quantitation and isolation of cannabinoids from *Cannabis sativa* L. by overpressured layer chromatography, Journal of Chromatography A, 388, 217-224 (1987), the disclosures of which are incorporated herein by reference in their entireties. In particular embodiments, the extraction method is chosen to provide an extract that has a content of myrcene, optional selected cannabinoids, and optional selected terpenes that best approximates the predetermined composition of the active ingredient.

In some embodiments, the process further comprises a first step of selecting a *Cannabis* sativa strain for subsequent development as a therapeutic agent or a source of extracted compounds for therapy.

In certain embodiments, the strain selected has a typical content in the plant as a whole, or in an extractable portion thereof, of myrcene, optional selected cannabinoids, and optional selected terpenes that best approximates the predetermined composition of the active ingredient. In certain embodiments, the strain selected is one that is capable of providing an extract that best approximates the predetermined composition of the active ingredient. In specific embodiments, the strain selected has a typical content in the plant, extractable portion thereof, or extract thereof, that best approximates the predetermined weight ratios of desired myrcene, selected cannabinoids, and selected terpenes. In specific embodiments, the strain selected has a typical content in the plant, extractable portion thereof, or extract thereof, that requires adjustment in concentration of the fewest number of the desired myrcene, selected cannabinoids, and selected terpenes. In specific embodiments, the strain selected has a typical content in the plant, extractable portion thereof, or extract thereof, that requires the least expensive adjustment in concentration of the desired myrcene, selected cannabinoids, and selected terpenes.

4.6. Product by Process

In typical embodiments, the pharmaceutically active ingredient is prepared by one of the processes described in Section 4.5 above.

In embodiments in which the pharmaceutically active ingredient is prepared from a starting compositional mixture by adjusting to predetermined desired final concentrations any one or more of myrcene, optional selected cannabinoids, and optional selected terpenes, all compounds in the active ingredient other than myrcene, selected cannabinoids, and selected terpenes are present within the starting compositional mixture. In embodiments in which the starting compositional mixture is a *Cannabis sativa* extract, all compounds in the active ingredient other than myrcene, selected cannabinoids, and selected terpenes are present within the *Cannabis sativa* extract.

4.7. Dose Ranges, Generally

In vivo and/or in vitro assays may optionally be employed to help identify optimal dosage ranges for use. The precise dose to be employed in the formulation will also depend on the route of administration, and the seriousness of the condition, and should be decided according to the judgment of the practitioner and each subject's circumstances. Effective doses may be extrapolated from dose-response curves derived from in vitro or animal model test systems.

4.8. Unit Dosage Forms

The pharmaceutical compositions may conveniently be presented in unit dosage form.

The unit dosage form will typically be adapted to one or more specific routes of administration of the pharmaceutical composition.

In various embodiments, the unit dosage form is adapted for administration by inhalation. In certain of these embodiments, the unit dosage form is adapted for administration by a vaporizer. In certain of these embodiments, the unit dosage form is adapted for administration by a nebulizer. In certain of these embodiments, the unit dosage form is adapted for administration by an aerosolizer.

In various embodiments, the unit dosage form is adapted for oral administration, for buccal administration, or for sublingual administration.

In some embodiments, the unit dosage form is adapted for intravenous, intramuscular, or subcutaneous administration.

In some embodiments, the unit dosage form is adapted for intrathecal or intracerebroventricular administration.

In some embodiments, the pharmaceutical composition is formulated for topical administration.

The amount of active ingredient which can be combined with a carrier material to produce a single dosage form will generally be that amount of the compound which produces a therapeutic effect.

4.9. Methods of Treatment

4.9.1. Methods of Effecting TRPV1 Desensitization in Cells of a Mammalian Subject We have demonstrated that the myrcene-containing compositions described herein have acute agonistic effects and long-term desensitization effects on TRPV1. These compositions can therefore have therapeutic effects mediated through TRPV1, either by acutely activating TRPV1, desensitizing TRPV1 by chronic application, or both. Furthermore, we have identified specific combinations of myrcene and selected cannabinoids and/or selected terpenes that exert significant additive or synergistic effects on TRPV1.

Accordingly, methods are presented for effecting TRPV1 desensitization in cells of a mammalian subject, the method comprising administering to the subject the myrcene-containing pharmaceutical compositions described herein in an amount, by a route of administration, and for a time sufficient to cause TRPV1 desensitization in cells within the subject.

In various embodiments, the pharmaceutical composition is administered topically.

In various embodiments, the pharmaceutical composition is administered systemically. In some embodiments, the pharmaceutical composition is administered orally, by buccal administration, or sublingually.

In some embodiments, the pharmaceutical composition is administered parenterally. In certain embodiments, the pharmaceutical composition is administered intravenously. In some embodiments, the pharmaceutical composition is administered subcutaneously. In some embodiments, the pharmaceutical composition is administered by inhalation.

These methods are particularly aimed at therapeutic and prophylactic treatments of mammals, and more particularly, humans.

The actual amount administered, and rate and schedule of administration, will depend on the nature and severity of disease being treated. Prescription of treatment, e.g. decisions on dosage etc., is within the responsibility of general practitioners and other medical professionals, and typically takes account of the disorder to be treated, the condition of the individual patient, the route of administration, the site to be treated, and other factors known to practitioners.

Examples of the techniques and protocols mentioned above can be found in Remington's Pharmaceutical Sciences, 16th edition, Osol, A. (ed), 1980.

In vivo and/or in vitro assays may optionally be employed to help identify optimal dosage ranges for use and routes and times for administration. The precise dose to be employed in the formulation will also depend on the route of administration, and the seriousness of the condition, and should be decided according to the judgment of the practitioner and each subject's circumstances. Effective doses and methods of administration may be extrapolated from dose-response curves derived from in vitro or animal model test systems.

In some embodiments, myrcene is administered in an amount less than 1 g, less than 500 mg, less than 100 mg, less than 10 mg per dose.

In the methods of treatment described herein, the myrcene-containing pharmaceutical composition can be administered alone or in combination with other treatments administered either simultaneously or sequentially with the myrcene-containing composition.

4.9.2. Methods of Treating Pain

In some embodiments, the cells to be subjected to TRPV1 desensitization are nociceptors, and the method comprises administering to the subject the myrcene-containing pharmaceutical compositions described herein in an amount, by a route of administration, and for a time sufficient to cause TRPV1 desensitization in nociceptors within the subject.

In some embodiments, the nociceptors are peripheral nociceptors. In certain of these embodiments, the pharmaceutical composition is administered topically. In some embodiments, the pain-sensing neurons are visceral. In certain of these embodiments, the pharmaceutical composition is administered systemically.

Our in silico analyses using the GB Sciences Network Pharmacology Platform, described below in Example 8, indicates that therapeutic efficacy of myrcene will likely extend beyond TRPV1 to other nociceptive neurons in which the primary pain-conducting channel is a distinct TRP.

Accordingly, in a related aspect, methods are provided for treating pain in a mammalian subject. The method comprises administering to the subject the myrcene-containing pharmaceutical compositions described herein in an amount, by a route of administration, and for a time sufficient to reduce pain.

In certain embodiments, the pain is neuropathic pain. In particular embodiments, the neuropathic pain is diabetic peripheral neuropathic pain. In particular embodiments, the pain is post-herpetic neuralgia. In particular embodiments, the pain is trigeminal neuralgia.

In some embodiments, the subject has pain related to or caused by strains, sprains, arthritis or other joint pain, bruising, backaches, fibromyalgia, endometriosis, surgery, migraine, cluster headaches, psoriasis, irritable bowel syndrome, chronic interstitial cystitis, vulvodynia, trauma, musculoskeletal disorders, shingles, sickle cell disease, heart disease, cancer, stroke, or mouth sores or ulceration due to chemotherapy or radiation.

In some embodiments, the pharmaceutical composition is administered at least once a day for at least 3 days. In some embodiments, the pharmaceutical composition is administered at least once a day for at least 5 days. In some embodiments, the pharmaceutical composition is administered at least once a day for at least 7 days. In some embodiments, the pharmaceutical composition is administered at least once a day for more than 7 days.

In various embodiments, the pharmaceutical composition is administered at a dose, by a route of administration, and on a schedule sufficient to maintain effective levels of myrcene at the nociceptors for at least 3 days, at least 5 days, or at least 7 days.

4.9.3. Methods of Treating Cardiac Hypertrophy

In another aspect, methods of treating cardiac hypertrophy in a mammalian subject are provided. The methods comprise administering to the subject an anti-hypertrophic effective amount of the myrcene-containing pharmaceutical compositions described herein.

In typical embodiments, the pharmaceutical composition is administered systemically.

In some embodiments, the pharmaceutical composition is administered intravenously. In some embodiments, the pharmaceutical composition is administered subcutaneously. In some embodiments, the pharmaceutical composition is administered by inhalation. In some embodiments, the pharmaceutical composition is administered orally.

4.9.4. Methods of Prophylactic Treatment for Cardiac Hypertrophy

In another aspect, methods of prophylactic treatment for cardiac hypertrophy in a mammalian subject are provided. The methods comprise administering to a subject at risk of cardiac hypertrophy an anti-hypertrophic effective amount of the myrcene-containing pharmaceutical compositions described herein.

4.9.5. Methods of Treating Overactive Bladder

In another aspect, methods of treating overactive bladder in a mammalian subject, are provided. The methods comprise administering to the subject a therapeutically effective amount of the myrcene-containing pharmaceutical compositions described herein.

In typical embodiments, the pharmaceutical composition is administered systemically.

4.9.6. Methods of Treating Refractory Chronic Cough

In another aspect, methods of treating refractory chronic cough are provided, the methods comprising administering to the subject a therapeutically effective amount of the myrcene-containing pharmaceutical composition described herein.

In some embodiments, the pharmaceutical composition is administered systemically.

In some embodiments, the pharmaceutical composition is administered by inhalation.

4.9.7. Methods of Treating Disorders with TRPV1 Etiology

In another aspect, diseases or disorders that are treated with the myrcene-containing pharmaceutical compositions described herein include diseases related to abnormal function of TRPV1. The diseases can be related to abnormal activation, suppression, or dysregulation of TRPV1. In some embodiments, the diseases are related to abnormal expression or mutation of the gene encoding TRPV1.

In some embodiments, diseases treated with the myrcene-containing pharmaceutical compositions described herein are diseases related to abnormal synthesis of an endogenous TRPV1 agonist.

4.10 EXAMPLES

The following examples are provided by way of illustration not limitation.

4.10.1. Example 1: Mixtures Comprising Terpenes, Cannabinoids, and Both Terpenes and Cannabinoids We prepared a complex mixture of cannabinoids and terpenes, the Strain A Mixture, based upon the actual chemo-profile of a Cannabis sativa cultivar currently used medicinally in Nevada, USA. Strain chemo-profile data was expressed as % mass and mg/g abundance, and these amounts were converted to amounts to be included in the mixture. The actual chemo-profile was modified in the Strain A Mixture by deliberate omission of THC and THCA and omission of certain labile or insoluble components. We also prepared complex mixtures containing subsets of the compounds in the Strain A Mixture: CBMIX, Cannabinoid Mixture and Terpene Mixture.

All mixtures were prepared by mixing individual components as specified below in Table 1. The Table provides percentage ratios of individual components by weight included in each mixture (Ratio, %). It also provides final concentrations of each component applied to the cell culture in the experiments described below (Conc., μg/ml).

Individual components were obtained from various vendors—for example, nerolidol from Tokyo Chemical Industry (#N0454), linalool from Tokyo Chemical Industry (#L0048), alpha-pinene from Sigma Aldrich (#P45680), limonene from MP Biomedicals (#155234), phytol from Ultr Scientific (#FLMS-035), cannabidivarin from Sigma Aldrich (#C-140), cannabichromene from Sigma Aldrich (#C-143), cannabidiol from Sigma Aldrich (#C-045), cannabigerol from Sigma Aldrich (#C-141) and cannabinol from Sigma Aldrich (#C-046). Myrcene, manufactured by MP Biomedical, was obtained from VWR, product #M0235. Each component was mixed as specified above in Table 1.

4.10.2. Example 2: Cell Culture System for Testing TRPV1-Mediated Calcium Response The HEK293 cell line was stably transfected with the pcDNA6TR (Invitrogen, CA) plasmid (encoding the tetracycline-sensitive TREx repressor protein), and was maintained in DMEM+10% fetal bovine serum (inactivated at 55° C. for 1 h)+2 mM glutamine in humidified 5% $CO_2$ atmosphere at 37° C. Selection pressure on the TRex 293 cells was maintained by continuous culture in 10 μg/ml Blasticidin (Sigma, St Louis, Mo.).

For production of TRex HEK293 cells with inducible expression of TRPV1, parental cells were electroporated with the rat TRPV1 cDNA in the pcDNA4TO vector and clonal cell lines were selected by limiting dilution in the presence of 400 μg/ml zeocin (Invitrogen, CA). TRPV1 expression was induced using 1 μg/ml tetracycline for 16 h

TABLE 1

| | Strain A Mixture | | CBMIX | | Cannabinoid Mixture | | Terpene Mixture | |
|---|---|---|---|---|---|---|---|---|
| | Ratio (%) | Conc. (μg/ml) | Ratio (%) | Conc. (μg/ml) | Ratio (%) | Conc. (μg/ml) | Ratio (%) | Conc. (μg/ml) |
| Cannabidivarin (CBDV) | 7.42 | 5.6 | 8.40 | 5.6 | 14.56 | 5.6 | 0.00 | 0 |
| Cannabichromene (CBC) | 1.92 | 1.45 | 2.17 | 1.45 | 3.77 | 1.45 | 0.00 | 0 |
| Cannabidiol (CBD) | 7.29 | 5.5 | 8.25 | 5.5 | 14.30 | 5.5 | 0.00 | 0 |
| Cannabidiolic Acid (CBDA) | 4.57 | 3.45 | 5.17 | 3.45 | 8.97 | 3.45 | 0.00 | 0 |
| Cannabigerol (CBG) | 3.64 | 2.75 | 4.12 | 2.75 | 7.15 | 2.75 | 0.00 | 0 |
| Cannabigerolic Acid CBGA) | 24.52 | 18.5 | 27.74 | 18.5 | 48.11 | 18.5 | 0.00 | 0 |
| Cannabinol (CBN) | 1.59 | 1.2 | 1.80 | 1.2 | 3.12 | 1.2 | 0.00 | 0 |
| alpha-Bisabolol | 2.58 | 1.95 | 2.92 | 1.95 | 0.00 | 0 | 5.27 | 1.95 |
| alpha-Humulene | 6.03 | 4.55 | 6.82 | 4.55 | 0.00 | 0 | 12.30 | 4.55 |
| α-Pinene | 0.66 | 0.5 | 0.75 | 0.5 | 0.00 | 0 | 1.35 | 0.5 |
| β-Caryophyllene | 14.18 | 10.7 | 16.04 | 10.7 | 0.00 | 0 | 28.92 | 10.7 |
| beta-Myrcene | 11.60 | 8.75 | 0.00 | 0 | 0.00 | 0 | 23.65 | 8.75 |
| (+)-beta-Pinene | 1.33 | 1 | 1.50 | 1 | 0.00 | 0 | 2.70 | 1 |
| Camphene | 0.20 | 0.15 | 0.22 | 0.15 | 0.00 | 0 | 0.41 | 0.15 |
| Limonene | 7.09 | 5.35 | 8.02 | 5.35 | 0.00 | 0 | 14.46 | 5.35 |
| Linalool | 2.39 | 1.8 | 2.70 | 1.8 | 0.00 | 0 | 4.86 | 1.8 |
| Nerolidol | 2.85 | 2.15 | 3.22 | 2.15 | 0.00 | 0 | 5.81 | 2.15 |
| Ocimene | 0.13 | 0.1 | 0.15 | 0.1 | 0.00 | 0 | 0.27 | 0.1 | at 37° C. Stable lines were screened for inducible protein expression using anti-FLAG Western blot, and inducible expression was confirmed. Electrophysiological measurements further confirmed the presence and UV curve 'signature' of TRPV1 in these induced cells. Furthermore, capsaicin-specific calcium fluxes provided in FIG. 1 also confirmed expression and specific response of TRPV1 in the cells, because the calcium flux was not detected in HEK wild type cells without a construct encoding TRPV1.

Calcium responses mediated by TRPV1 were tested by calcium assay in the cell culture system. Cells were washed and incubated with 0.2 μM fluo-4 acetoxymethyl ester ("Fluo-4") for 30 minutes at 37° C. in a standard modified Ringer's solution of the following composition (in mM): NaCl 145, KCl 2.8, CsCl 10, CaCl2 10, MgCl2 2, glucose 10, Hepes.NaOH 10, pH 7.4, 330 mOsm. Cells were transferred to 96-well plates at 50,000 cells/well and stimulated as indicated. Calcium signals were acquired using a Flexstation 3 (Molecular Devices, Sunnydale, USA). Data was analyzed using SoftMax® Pro 5 (Molecular Devices). Where indicated, nominally calcium-free external conditions were achieved by the preparation of 0 mM $CaCl_2$ Ringer solution containing 1 mM EGTA. Where indicated, capsaicin (10 μM) and ionomycin (500 nM) were used as positive controls to induce calcium responses. Capsazepine (10 μM) was used where indicated to specifically antagonize TRPV1-mediated calcium responses. Where indicated, baseline traces (no stimulation, NS) were subtracted. Where indicated, vehicle alone traces were subtracted. Where indicated, vehicle comprising various diluents matched to corresponding mixtures was used as a negative control.

4.10.3. Example 3: TRPV1-Mediated Calcium Influx in Response to Strain A Mixture, Cannabinoid Mixture, or Terpene Mixture TRPV1-mediated calcium influx was tested in response to the Strain A Mixture, Cannabinoid Mixture and Terpene Mixture as described above. Each mixture was applied to the cell culture medium to expose the cells to final concentrations of individual components as provided in Table 1 ("Conc. μg/ml"). For example, the Strain A Mixture was applied to expose the cells to 5.6 μg/ml of cannabidivarin (CBDV), 8.75 μg/ml of myrcene, etc.

FIGS. 2A-C provide calcium flux data measured as Fluo-4 relative fluorescence unit (Fluo-4 RFU) over time (sec). As provided in FIGS. 2A-C, significant calcium fluxes were observed in response to application of the Strain A Mixture (FIG. 2A), and the Terpene Mixture (FIG. 2C), but less so in response to application of the Cannabinoid Mixture (FIG. 2B). The calcium fluxes were not detected in the absence of stimuli ("NS") or in response to application of vehicle ("veh") (FIGS. 2A-C).

When wild-type HEK cells without the TRPV1 construct were presented with the same stimulus conditions, calcium fluxes were not observed (FIGS. 5A-5C). These data demonstrate that the calcium influxes in response to the Strain A Mixture, the Cannabinoid Mixture, or the Terpene Mixture are specific to and mediated by TRPV1.

4.10.4. Example 4: TRPV1-Mediated Calcium Influx in Response to Individual Terpenes Because the Terpene Mixture was identified in Example 3 to be largely responsible for the TRPV1-agonistic effects of the Strain A Mixture (see FIGS. 2A-2C), TRPV1-mediated calcium influx was tested in response to individual components of the Terpene Mixture. Each component was applied in the cell culture medium, while fluorescence signals were monitored. Fluorescence signals measured over time are presented in FIGS. 3B-3L for individual terpene compounds.

Significant calcium influx was detected in response to some, but not all, of the terpene compounds tested. In particular, significant calcium flux was detected in response to myrcene (FIG. 3D) and nerolidol (FIG. 3I).

When TRPV1-agonistic effects were compared between myrcene alone and the Terpene Mixture, myrcene was seen to contribute significantly to TRPV1-mediated calcium response, but did not account for 100% of the calcium influx signal. As shown in FIG. 4, the Terpene Mixture (solid curve) had more significant effects than myrcene alone (dotted curve). This suggests that some terpenes, including nerolidol, may have additive or synergistic effects on TRPV1 when applied with myrcene.

4.10.5. Example 5: Activation of TRPV1 by Myrcene

Myrcene's agonistic effects on TRPV1 were further tested under various conditions. First, TRPV1-mediated calcium flux was tested in response to different concentrations of myrcene (3.5 μm/ml, 1.75 μg/ml, 0.875 μm/ml and 0.43 μm/ml). As illustrated in FIGS. 6A-6D, calcium responses to myrcene were dose-dependent, with the largest flux in response to 3.5 μm/ml of myrcene and the smallest flux in response to 0.43 μg/ml of myrcene. The calcium flux was much smaller in the wild-type HEK cell culture (dotted curves in FIGS. 6A-6D), demonstrating that myrcene induces calcium flux through TRPV1 channel.

Myrcene's agonistic effects on TRPV1 was further confirmed by applying TRPV1 inhibitor, 10 μM of capsazepine, in the cells activated with 3.5 μm/ml myrcene. As provided in FIG. 7A, calcium flux induced by myrcene diminished in response to capsazepine. As shown in FIG. 7B, calcium flux did not change in response to PBS, applied as a control. The data demonstrate that myrcene induces calcium flux by activating TRPV1.

Figure 8A:
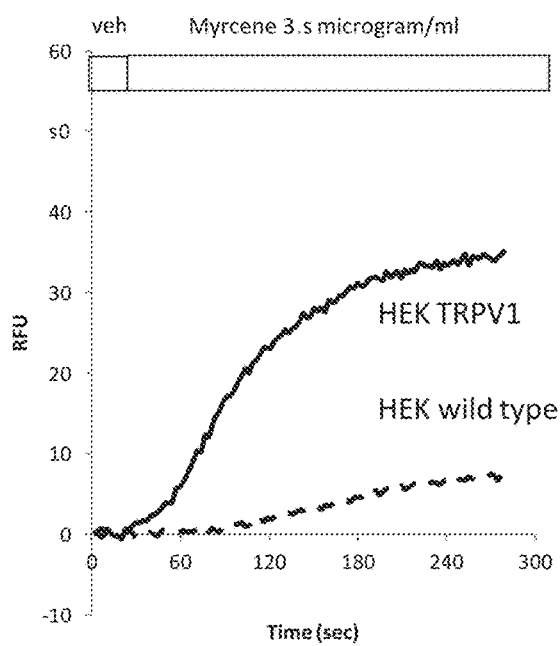
Figure 8B:
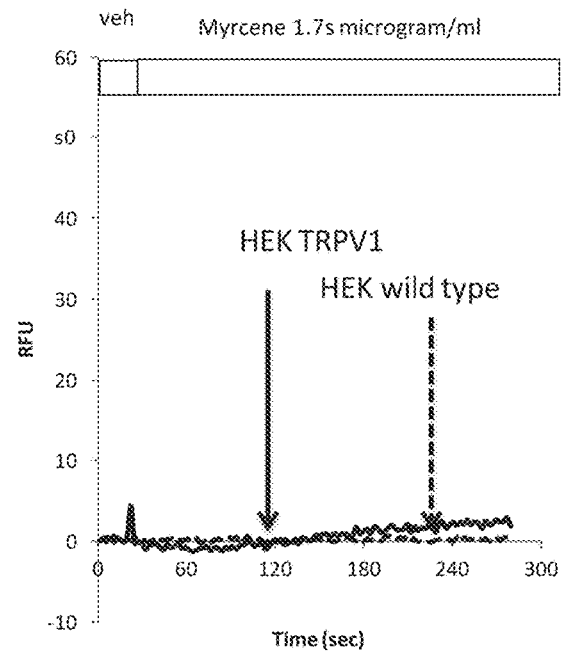
Figure 8C:
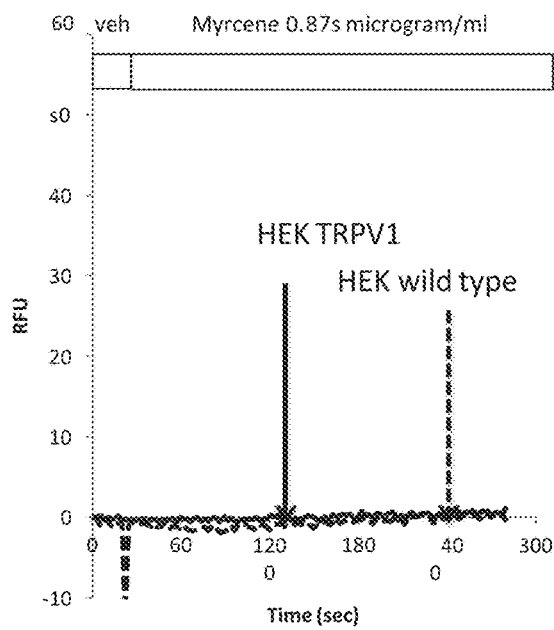
Figure 8D:
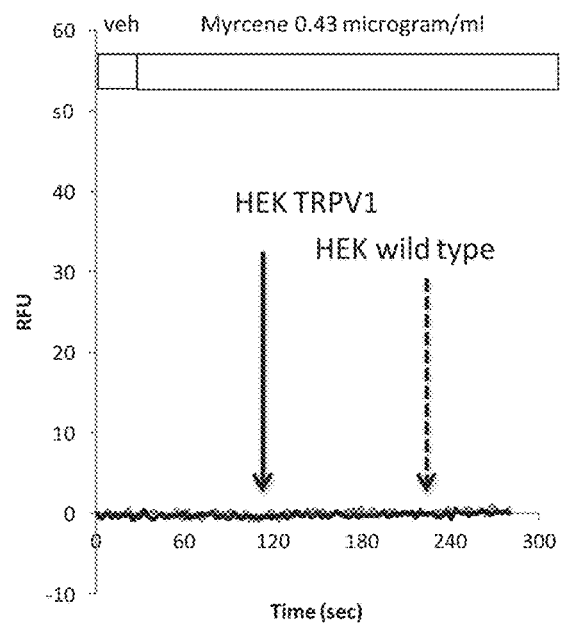
Figure 9A:
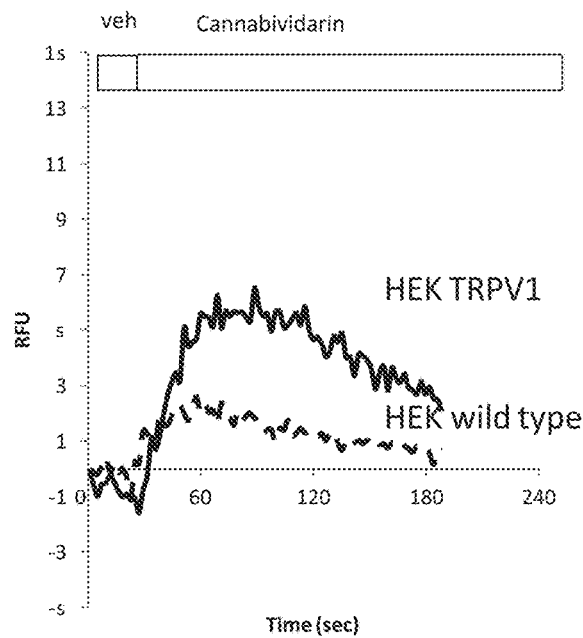
Figure 9B:
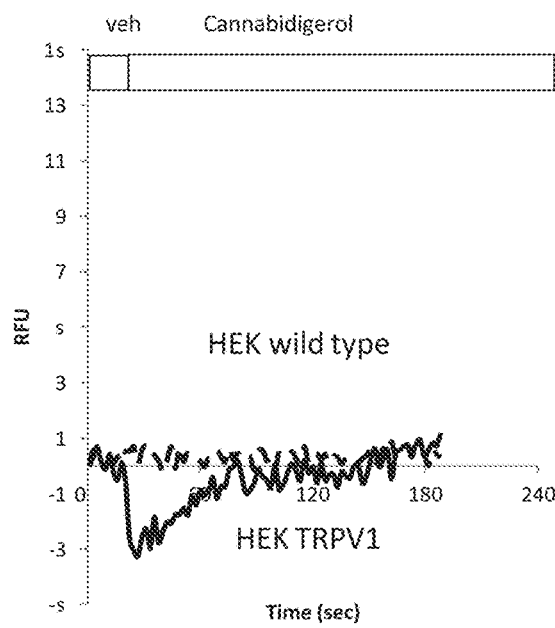
Figure 9C:
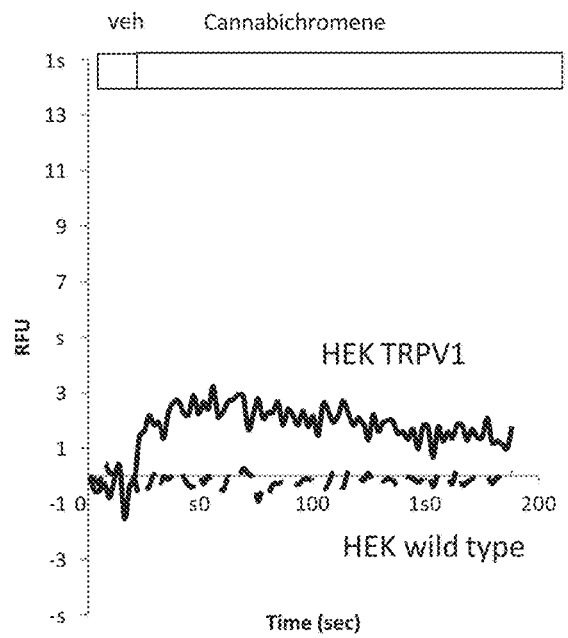
Figure 9D:
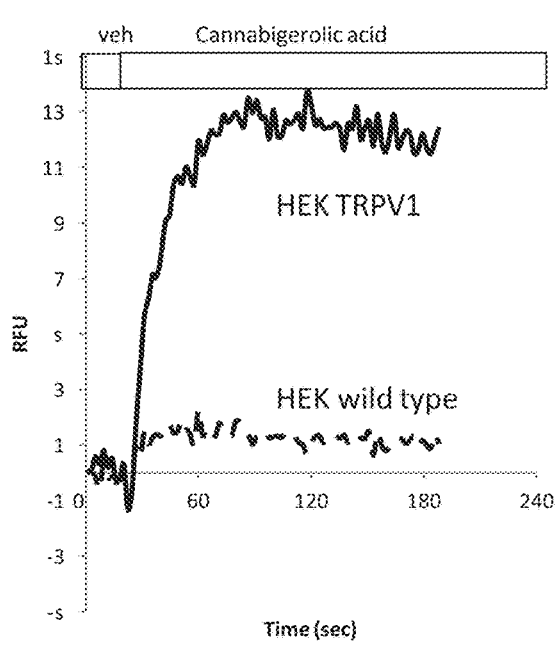
Figure 9E:
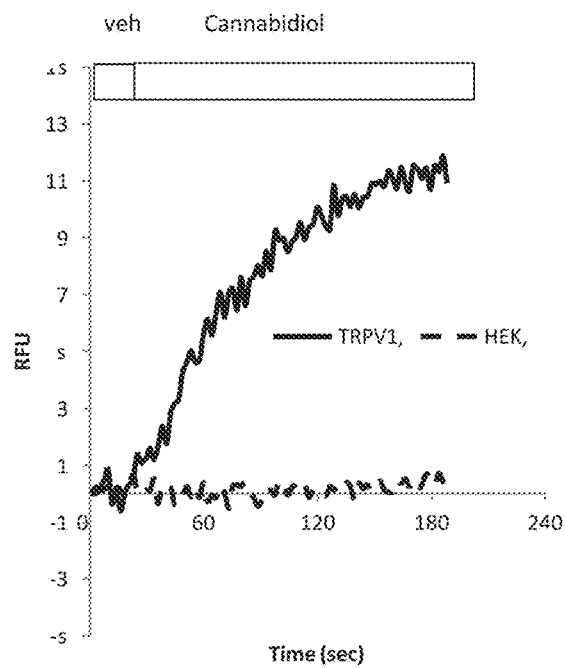
Figure 9F:
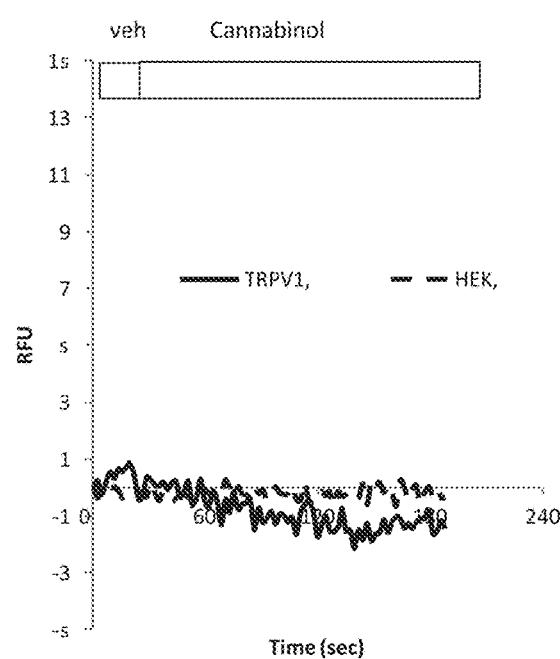
Figure 9G:
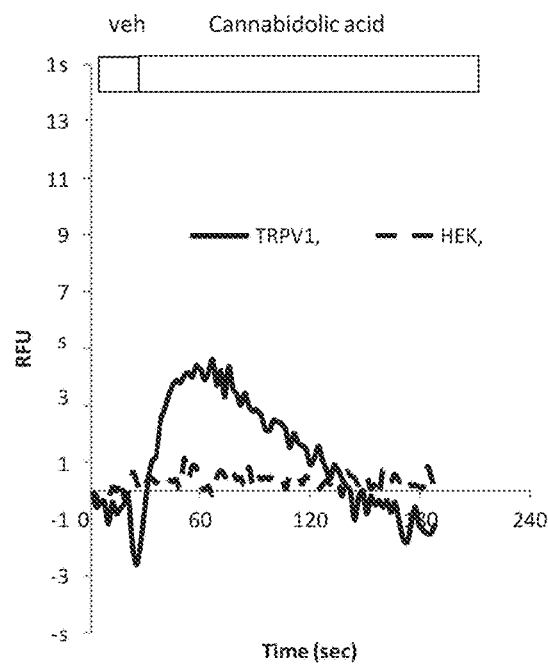

Activation of TRPV1 by myrcene was also tested under calcium-free medium conditions. Under these conditions, low concentrations of myrcene (0.43 μg/ml, 0.875 μg/ml and 1.75 μg/ml) did not cause increase of calcium-mediated fluorescence (see FIGS. 8B, 8C, 8D), whereas a high concentration of myrcene (3.5 μg/ml) induced such increase (FIG. 8A). This suggests that myrcene induces calcium flux mostly from extracellular buffer at low concentrations, but can induce calcium flux into the cytosol from intracellular stores at high concentrations. Both extracellular and intracellular fluxes rely on TRPV1, since calcium influx was not observed or were only minimal in wild-type HEK cells without TRPV1 (dotted curves in FIGS. 8A-8D).

To confirm and further investigate the activation of TRPV1 by myrcene, channel currents were assessed via patch clamp experiments in single HEK293 cells overexpressing rat TRPV1. HEK293 cells were kept in sodium-based extracellular Ringer's solution containing 140 mM NaCl, 1 mM $CaCl_2$, 2 mM $MgCl_2$, 2.8 mM KCl, 11 mM glucose, and 10 mM HEPES-NaOH, pH 7.2 and osmolarity 300 mOsmol. The cells' cytosol was perfused with intracellular patch pipette solution containing 140 mM Cs-glutamate, 8 mM NaCl, 1 mM $MgCl_2$, 3 mM MgATP, and 10 mM HEPES-CsOH. The standard internal $Ca^{2+}$ concentration was buffered to 180 nM with 4 mM Ca and 10 mM BAPTA. The level of free unbuffered Ca was adjusted using the calculator provided with WebMaxC (http://www.stanford.edu/~cpatton/webmaxcS.htm). The pH of the final solution was adjusted to pH 7.2 and osmolarity measured at 300 mOsmol.

TRPV1 channels were activated by adding 5 µM, 10 µM, or 150 µM myrcene to the extracellular solution. 1 µM capsaicin was used as a positive control for TRPV1 activation. Rapid extracellular solution application and exchange was performed with the SmartSquirt delivery system (AutoMate Scientific, San Francisco). The system includes a ValveLink TTL interface between the electronic valves and the EPC-9 amplifier (HEKA, Lambrecht, Germany). This configuration allows for programmable solution changes via the PatchMaster software (HEKA, Lambrecht, Germany).

Patch-clamp experiments were performed in the whole-cell configuration at 21-25° C. Patch pipettes had resistances of 2-3 MΩ. Data was acquired with PatchMaster software controlling an EPC-9 amplifier. Voltage ramps of 50 ms spanning the voltage range from −100 to 100 mV were delivered from a holding potential of 0 mV at a rate of 0.5 Hz over a period of 500 ms. Voltages were corrected for a liquid junction potential of 10 mV. Currents were filtered at 2.9 kHz and digitized at 100 µs is intervals. Capacitive currents were determined and corrected before each voltage ramp. The development of currents for a given potential was extracted from individual ramp current records by measuring the current amplitudes at voltages of −80 mV and +80 mV. Data were analyzed with FitMaster (HEKA, Lambrecht, Germany), and IgorPro (WaveMetrics, Lake Oswego, Oreg., USA). Where applicable, statistical errors of averaged data are given as mean±s.e.m.

As shown in FIGS. 19A-19C, myrcene induced a dose-dependent response in individual cells. Inward and outward current development is shown over time. Each data point (DP) corresponds to approximately 1 second. 5 µM (FIG. 19A), 10 µM (FIG. 19B), and 150 µM (FIG. 19C) myrcene induced 0.5-2.2 nA current compared to 4-10 nA current induced by application of 1 µM capsaicin (not shown). Increasing doses of myrcene result in an inwardly rectifying non-selective cation current which inactivated in a manner dependent both on activation current amplitude (FIGS. 19A-19C) and calcium influx (data not shown).

FIG. 20 shows the same experiment as FIG. 19A, but with the addition of capsaicin after the myrcene application. HEK293 cells overexpressing rat TRPV1 were equilibrated in extracellular Ringer's solution containing 1 mM Ca. The extracellular buffer was exchanged for buffer containing 5 µM myrcene at datapoint (DP) 60. The myrcene solution was exchanged for extracellular buffer containing 1 µM capsaicin at DP 120. Inward and outward currents (nA) were measured at each DP. FIG. 20A shows the average inward and outward currents of 6 independent experiments. 5 µM myrcene induced an approximately 0.5 nA inward current over time, while 1 µM capsaicin induced an approximately 9 nA inward current. Both myrcene and capsaicin also induced an outward current at a lower amplitude than the inward current. FIG. 20B shows a magnified view of the myrcene-induced current.

Next, the relationship between the myrcene- and capsaicin-induced current and the experimental voltage was analyzed. Voltage ramps were performed at data points 1, 59, 119, and 179 (FIG. 20A, arrows 1-4 IV), and the IV relationship assessed before and after addition of myrcene and capsaicin (FIGS. 20C-E). FIG. 20C shows the break-in current ("1 IV" on FIG. 20A) of the cell and the early current development ("2 IV" on FIG. 20A) in the presence of Ringer's solution. FIG. 20D shows the myrcene-induced TRPV1 activation ("3 IV" on FIG. 20A). FIG. 20E shows the capsaicin-induced TRPV1 activation ("4 IV" on FIG. 20A).

Capsaicin is a TRPV1 agonist known to selectively increase $Ca^{2+}$ ion permeability of the TRPV1 channel. The channel's permeation properties have been previously documented in two states. State 1 for this non-selective cation channel (NSCC) is marginal or no selectivity for calcium over sodium. State 2 (the dilated or transition state) represents an attained state where pore properties have changed to permeate large cations (for example NMDG) and support correspondingly large fluxes of calcium and sodium. The transition from State 1 to State 2 is characterized by a marked linearization of the IV curve with correspondingly larger inward currents than in State 1. FIG. 19 and FIG. 20 shows that myrcene is a strong activator of TRPV1, producing nA currents. In contrast to capsaicin, myrcene activates the channel primarily in State 1. The differences between the myrcene-induced and capsaicin-induced TRPV1 activation properties suggest that the amplitude, selectivity and therefore physiological outcomes of TRPV1 activation can be manipulated in a rational manner based on differential electrophysiological characteristics of TRPV1-mediated responses to myrcene as opposed to the conventional ligand capsaicin.

4.10.6. Example 6: Effects of Non-Myrcene Components of the Strain A Mixture on TRPV1

Since myrcene alone could not explain all the TRPV1 agonistic effects of the Strain A Mixture, effects of individual cannabinoids and CBMIX (i.e., the Strain A Mixtures not including myrcene) on TRPV1 were further studied to understand the remaining TRPV1-agonistic effects of the Strain A Mixture.

First, individual cannabinoids were applied in the cell culture medium, while fluorescence signals were monitored. FIGS. 9A-9G illustrate that cannabinoids differentially contribute to calcium fluxes via TRPV1. Modest calcium responses were detected in response to some, but not all, cannabinoid compounds. In particular, calcium flux was detected in response to cannabidivarin (CBDV), cannabichromene (CBC), cannabidiol (CBD), cannabidiolic acid (CBDA), and cannabigerolic acid (CBGA). Such calcium responses were only minimal or absent in cells without TRPV1, demonstrating that the calcium response is mediated by TRPV1.

Having observed that (i) myrcene contributes significantly to the TRPV1-mediated calcium response, but did not account for 100% of the calcium influx signal of the Terpene Mixture (FIG. 4); and (ii) that the Terpene Mixture in turn contributes to the TRPV1-mediated calcium response, but did not account for 100% of the calcium influx signal of the Strain A Mixture (FIGS. 2A-2C), we tested whether a mixture of cannabinoids and terpenes of the Strain A Mixture excluding myrcene ("CBMIX"), affected multidrug resistance protein (MRP)-mediated export of myrcene, the bioactive ligand. As provided in FIG. 10, application of CBMIX significantly suppressed MRP-mediated export of fluorescent marker CFDA. Not wishing to be bound by a theory, this suggests that the mixture of terpenes and cannabinoids in CBMIX can enhance TRPV1-agonistic effects of myrcene by blocking MRP-mediated export of myrcene. For example, CBMIX can delay the efflux of myrcene from the cell and increase the specific activity of myrcene per unit dose.

4.10.7. Example 7: Desensitization of TRPV1 by Myrcene

TRPV1-agonistic effects of myrcene and capsaicin were compared in various concentrations. Specifically, area under curve (AUC) of the calcium response curve for myrcene and capsaicin were separately calculated and plotted over corresponding concentrations in FIG. 14A. Higher concentrations of myrcene were needed to induce the same calcium influx as capsaicin. For example, about 200 nM of myrcene and about 30 nM capsaicin induced calcium influx to a similar degree, when the degree of calcium influx is determined based on the AUC between 20 and 300 nM of their calcium response curves.

Long-term effects on TRPV1 were also compared between myrcene and capsaicin. As provided in FIG. 14B, both myrcene and capsaicin induced desensitization of TRPV1 after exposure to each compound for 24 hours. For example, when myrcene was first introduced to TRPV1-expressing cells, myrcene induced calcium flux to generate a response curve with AUC (between 20-300 nM) of 66. However, after the cells were incubated with myrcene for 24 hours, myrcene induced calcium response with AUC of 32. Thus, pre-incubation with myrcene suppressed later calcium response by 52%. Similarly, when capsaicin was first introduced to TRPV1-expressing cells, capsaicin induced calcium influx to generate a response curve with AUC of 124. After the cells were incubated with capsaicin for 24 hours, capsaicin induced calcium response with AUC of 38. Thus, pre-incubation with capsaicin suppressed later calcium response by 69%.

Long-term desensitization effects of myrcene and capsaicin on TRPV1 were compared with long-term effects of ionomycin as a control compound. As with myrcene or capsaicin, an initial application of ionomycin induced calcium influx to generate a response curve with AUC of 128. However, long-term desensitization effects of ionomycin were smaller than myrcene or capsaicin. As provided in FIG. 14B, pre-incubation with 500 nM of ionomycin reduced later calcium influx in response to myrcene or capsaicin only by 27% or 38%, respectively.

The data suggest that myrcene is an effective TRPV1 agonist that works in a similar way as capsaicin. Myrcene can induce TRPV1-mediated calcium influx after a short exposure, and desensitization of TRPV1 after a prolonged exposure. This suggests that myrcene can be used as an effective TRPV1 agonist to treat various diseases associated with TRPV1, and for which capsaicin is currently used for treatment. Myrcene can replace capsaicin as a pharmaceutically active ingredient for various indications.

4.10.8. Example 8: Network Pharmacology Platform

In order to assess whether myrcene and nerolidol, the two terpenes in our original *Cannabis* Strain A Mixture with significant TRPV1 agonist effects, had effects at other TRP channels, we developed an in silico prediction approach, termed the GB Sciences Network Pharmacology Platform.

Node and edge data was pulled from the http://bio-net.ncpsb.org/batman-tcm/ result page source. The data contain source and target information as well as group assignments used to generate Cytoscape network graphs on the website. The node and edge text files were loaded into the R statistical analysis program as comma separated files (csv). Files were cleaned of superfluous labeling and special characters and then arranged into node and edge data frames with clearly defined variable columns and observation rows using the dplyr library. Node data was reassigned group designations as per the Batman assignments and sorted in alpha order also using the dplyr library. The edge data frame was used to generate a directed network data object using the network library. The network object has two variables added to it: (i) the sorted group assignments from the node data frame, and (ii) the Freeman degree attribute which is calculated from the edge list and assigned to each node using the sna library. Network graphing was rendered through graphing interpreters from the ggnetwork and ggrepel libraries, which render graphs from the network object and use formatting arguments for style.

FIG. 16A shows the target analysis and disease-prediction network for myrcene. The presence of multiple TRP channels in the network indicates that efficacy of myrcene will likely extend beyond TRPV1 to other nociceptive neurons in which the primary pain-conducting channel is a distinct TRP. FIG. 16B shows the target analysis and disease-prediction network for nerolidol. The presence of multiple TRP channels in the network indicates that efficacy of nerolidol does not significantly add TRP channels for which myrcene is not indicated.

FIG. 11 illustrates that Therapeutic Target Database (TD) enrichment analysis tends to prioritize myrcene over nerolidol for development in pain and cardiovascular indications. In addition, myrcene contributes significantly to the predicted disease target set for native *Cannabis*.

FIG. 12 illustrates that diverse ion channel targets are predicted for direct or indirect modulation by myrcene.

INCORPORATION BY REFERENCE

All publications, patents, patent applications and other documents cited in this application are hereby incorporated by reference in their entireties for all purposes to the same extent as if each individual publication, patent, patent application or other document were individually indicated to be incorporated by reference for all purposes.

EQUIVALENTS

While various specific embodiments have been illustrated and described, the above specification is not restrictive. It will be appreciated that various changes can be made without departing from the spirit and scope of the invention(s). Many variations will become apparent to those skilled in the art upon review of this specification.

The invention claimed is:

1. A method of treating a disease in a mammalian subject, comprising:
   administering to the subject an effective amount of the pharmaceutical composition comprising:
   myrcene;
   at least one cannabinoid and/or terpene other than myrcene; and
   a pharmaceutically acceptable carrier or diluent,
   wherein the composition comprises no more than 20 different species from a total set of cannabinoid and terpene compounds, and is substantially free of THC, and
   wherein the disease is selected from the group consisting of cardiac hypertrophy, overactive bladder and refractory chronic cough.

2. The method of claim 1, wherein the pharmaceutical composition is administered systemically.

3. The method of claim 2, wherein the pharmaceutical composition is administered intravenously.

4. The method of claim 2, wherein the pharmaceutical composition is administered subcutaneously.

5. The method of claim 2, wherein the pharmaceutical composition is administered by inhalation.

6. The method of claim 2, wherein the pharmaceutical composition is administered orally.

7. The method of claim 1, wherein the disease is cardiac hypertrophy.

8. The method of claim 1, wherein the disease is overactive bladder.

9. The method of claim 1, wherein the disease is refractory chronic cough.

10. The method of claim 1, wherein the composition comprises no more than 15 species of terpene compounds.

11. The method of claim 1, wherein the composition comprises no more than 10 species of terpene compounds.

12. The method of claim 1, wherein myrcene is present in an amount that is at least 10%, 20%, 25%, 50%, 75%, or 90% (w/w) of the total content of terpenes.

13. The method of claim 1, wherein the at least one terpene other than myrcene is nerolidol.

14. The method of claim 1, wherein nerolidol is present in an amount that is at least 2% (w/w) of the total content of terpenes.

15. The method of claim 14, wherein nerolidol is present in an amount that is at least 2.5% (w/w) of the total content of terpenes.

16. The method of claim 15, wherein nerolidol is present in an amount that is at least 5% (w/w) of the total content of terpenes.

17. The method of claim 15, wherein the composition is administered at a dose, by a route of administration, and on a schedule sufficient to maintain effective levels of myrcene at the nociceptors for at least 3 days.

18. The method of claim 15, wherein the composition is administered at a dose, by a route of administration, and on a schedule sufficient to maintain effective levels of myrcene at the nociceptors for at least 7 days.

19. A method of treating refractory chronic cough in a mammalian subject, comprising:
   administering to the subject an effective amount of the pharmaceutical composition comprising:
      myrcene;
      optionally at least one cannabinoid and/or terpene other than myrcene; and
      a pharmaceutically acceptable carrier or diluent,
   wherein the composition comprises no more than 20 different species from a total set of cannabinoid and terpene compounds, and is substantially free of THC.

20. A method of treating a disease in a mammalian subject, comprising:
   administering to the subject an effective amount of the pharmaceutical composition comprising:
      myrcene;
      optionally at least one cannabinoid and/or terpene other than myrcene; and
      a pharmaceutically acceptable carrier or diluent,
   wherein the composition comprises no more than 20 different species from a total set of cannabinoid and terpene compounds, and is substantially free of THC, and
   wherein the disease is selected from the group consisting of cardiac hypertrophy, overactive bladder and refractory chronic cough, wherein the composition is administered at a dose, by a route of administration, and on a schedule sufficient to maintain effective levels of myrcene at the nociceptors for at least 3 days.

* * * * *